US007416903B2

(12) United States Patent
Sklar et al.

(10) Patent No.: US 7,416,903 B2
(45) Date of Patent: Aug. 26, 2008

(54) WAVY INTERFACE MIXER

(75) Inventors: Larry A. Sklar, Albuquerque, NM (US); Andrea A. Mammoli, Albuquerque, NM (US); Richard A. Truesdell, Albuquerque, NM (US); Peter V. Vorobieff, Albuquerque, NM (US)

(73) Assignee: STC.UNM, Albuquerque, NM (US)

(*) Notice: Subject to any disclaimer, the term of this patent is extended or adjusted under 35 U.S.C. 154(b) by 840 days.

(21) Appl. No.: 10/428,931

(22) Filed: May 5, 2003

(65) Prior Publication Data

US 2003/0207338 A1 Nov. 6, 2003

Related U.S. Application Data

(63) Continuation-in-part of application No. 10/247,439, filed on Sep. 20, 2002, now abandoned, and a continuation-in-part of application No. 10/021,243, filed on Dec. 19, 2001, which is a continuation-in-part of application No. 09/501,643, filed on Feb. 10, 2000, now Pat. No. 6,890,487.

(60) Provisional application No. 60/378,536, filed on May 6, 2002, provisional application No. 60/330,624, filed on Oct. 26, 2001, provisional application No. 60/156,946, filed on Sep. 30, 1999.

(51) Int. Cl.

| | |
|---|---|
| ***G01N 1/10*** | (2006.01) |
| ***G01N 1/00*** | (2006.01) |
| ***G01N 1/68*** | (2006.01) |
| ***G01N 15/06*** | (2006.01) |
| ***C12Q 33/00*** | (2006.01) |

(52) U.S. Cl. .......................... 436/180; 436/43; 436/52; 436/53; 436/63; 436/174; 422/50; 422/68.1; 422/100; 422/81; 422/82; 422/101; 137/87.01; 137/88; 137/109; 137/110; 137/111; 137/112

(58) Field of Classification Search .................. 422/50, 422/68.1, 100, 81, 82, 101; 436/43, 52, 53, 436/63, 174, 180; 137/87.01, 88, 109, 110, 137/111, 112
See application file for complete search history.

(56) References Cited

U.S. PATENT DOCUMENTS 3,640,822 A 2/1972 Hrdina (Continued)

OTHER PUBLICATIONS

Deandrade et al., "High Performance Modular Spectrophotometric Flow Cell," *Analyst*, v. 116:905-907, 1991.

(Continued)

*Primary Examiner*—Brian Sines
(74) *Attorney, Agent, or Firm*—R. Neil Sudol; Henry D. Coleman; William J. Sapone

(57) ABSTRACT

The present invention provides methods and apparatus for mixing samples in-line in a microfluidic system, comprising methods of and means for introducing a first fluid sample into a flow-tube at a first end at a first velocity via a first conduit; methods of and means for introducing a second fluid sample into the flow-tube at the first end at a second velocity, the second velocity different from the first velocity, via a second conduit, wherein the first fluid sample and the second fluid sample converge in the flow tube to form an interface; whereby the first fluid sample and the second fluid sample mix at the interface within the flow-tube, wherein fluid flow at the first end of the flow-tube is laminar and fluid flow at a second end of the flow-tube is laminar, and wherein the flow-tube has a constant diameter between the first end and the second end of the flow-tube.

24 Claims, 23 Drawing Sheets

U.S. PATENT DOCUMENTS

| | | | |
|---|---|---|---|
| 3,698,870 A | 10/1972 | DeJong | |
| 3,921,439 A | 11/1975 | Burns | |
| 4,053,282 A | 10/1977 | Hach et al. | |
| 4,116,631 A | 9/1978 | Trinel et al. | |
| 4,177,677 A | 12/1979 | Ruzicka et al. | |
| 4,224,033 A | 9/1980 | Hansen et al. | |
| 4,253,846 A | 3/1981 | Smythe et al. | |
| 4,399,225 A | 8/1983 | Hansen et al. | |
| 4,661,913 A | 4/1987 | Wu et al. | |
| 4,853,336 A | 8/1989 | Saros et al. | |
| 4,957,009 A | 9/1990 | Nohl et al. | |
| 5,062,419 A | 11/1991 | Rider | |
| 5,080,866 A | 1/1992 | Petty et al. | |
| 5,199,386 A | 4/1993 | Hubbard | |
| 5,221,521 A | 6/1993 | Hashizume et al. | |
| 5,225,488 A | 7/1993 | Baird et al. | |
| 5,250,104 A | 10/1993 | Berger et al. | |
| 5,251,662 A | 10/1993 | Rubel et al. | |
| 5,268,147 A | 12/1993 | Zabetakis et al. | |
| 5,286,452 A | 2/1994 | Hansen | |
| 5,369,037 A | 11/1994 | Hansen | |
| 5,374,398 A | 12/1994 | Isami et al. | |
| 5,395,588 A | 3/1995 | North et al. | |
| 5,407,274 A | 4/1995 | Woerheide et al. | |
| 5,464,752 A | 11/1995 | Kortright et al. | |
| 5,488,469 A | 1/1996 | Yamamoto et al. | |
| 5,504,010 A | 4/1996 | Mitani et al. | |
| 5,532,154 A | 7/1996 | Brown | |
| 5,641,457 A | 6/1997 | Vardanega et al. | |
| 5,694,486 A | 12/1997 | Shigeeda et al. | |
| 5,709,468 A | 1/1998 | Woerheide et al. | |
| 5,710,854 A | 1/1998 | Myers et al. | |
| 5,739,036 A | 4/1998 | Parris | |
| 5,776,781 A | 7/1998 | Varadanega et al. | |
| 5,788,927 A | 8/1998 | Farrell et al. | |
| 5,806,471 A | 9/1998 | Lin | |
| 5,810,032 A | 9/1998 | Hong et al. | |
| 5,824,269 A | 10/1998 | Kosaka et al. | |
| 5,834,314 A | 11/1998 | Gates et al. | |
| 5,895,764 A | 4/1999 | Sklar et al. | |
| 5,958,203 A | 9/1999 | Parce et al. | |
| 6,056,001 A | 5/2000 | Boyles et al. | |
| 6,132,685 A | 10/2000 | Kercso et al. | |
| 6,150,180 A | 11/2000 | Parce et al. | |
| 6,156,178 A | 12/2000 | Mansfield et al. | |
| 6,454,945 B1 * | 9/2002 | Weigl et al. | 210/634 |
| 6,541,213 B1 * | 4/2003 | Weigl et al. | 435/7.1 |
| 7,011,791 B2 * | 3/2006 | Weigl et al. | 422/58 |
| 7,141,429 B2 * | 11/2006 | Munson et al. | 436/53 |

OTHER PUBLICATIONS

Hodder, P. S., et al., "Microfabricated Flow Chamber for Fluorescence-Based Chemistries and Stopped-Flow Injection Cytometry," *Analyst*, vol. 122, pp. 883-887, (Sep. 1997).

Lindberg et al., "Flow Injection Cytometry: A New Approach for Sample and Solution Handling in Flow Cytometry," *Cytometry* 14:230-236 (1993).

Nolan, J. P., et al., "A Rapid Mix Flow Cytometer with Subsecond Kinetic Resolution," *Cytometry*, vol. 21, pp. 223-229 (1995).

Nolan, J. P., et al., "The Emergence of Flow Cytometry for Sensitive, Real-Time Measurements of Molecular Interactions," *Nature Biotechnology*, vol. 16, pp. 633-638 (Jul. 1998).

Pennings et al., "Improved Flow Cytometry of Cellular DNA and RNA by On-Line Reagent Addition," *Cytometry* 8:335-338 (1987).

Zhao et al., "A Flow Injection Flow Cytometry System for Online Monitoring of Bioreactors," *Biotechnology and Bioengineering* v62:609-617, *Analyst*.

Zhi ZL, "Segmental Flow-Injection Analysis, A Hybrid Technique of Segmented Continuous-Flow Analysis, a Hybrid Technique of Segmented Continuous-Flow Analysis and Flow-Injection Analysis," *Analysis*.

US 5,778,927, 8/1998, G. A. Farrell, et al. (withdrawn).

US 5,778,927, 8/1998, Farrell et al. (withdrawn).

* cited by examiner

WAVY INTERFACE MIXER

CROSS-REFERENCE TO RELATED APPLICATIONS

This application makes reference to and claims priority to the following U.S. patent applications. The first application is U.S. patent application Ser. No. 10/247,439, entitled "In-line Microfluidic Mixers for High Throughput Flow Cytometry" filed Sep. 20, 2002, which claims priority from U.S. Provisional Patent Application No. 60/330,624, entitled "In-line Microfluidic Mixers for High Throughput Flow Cytometry" filed Oct. 26, 2001. The second application is U.S. Provisional Patent Application No. 60/378,536, entitled "Drug Discovery Systems and Methods and Compounds for Drug Delivery" filed May 6, 2002. The third application is U.S. patent application Ser. No. 10/021,243, entitled "Microfluidic Micromixer" filed on Dec. 19, 2001. The fourth application is U.S. patent application Ser. No. 09/501,643, entitled "Flow Cytometry for High Throughput Screening" filed Feb. 10, 2000, which claims priority from U.S. Provisional Patent Application No. 60/156,946, entitled "Flow Cytometry Realtime Analysis for Molecular Interactions" filed on Sep. 30, 1999. The entire contents and disclosures of the above applications are hereby incorporated by reference.

GOVERNMENT INTEREST STATEMENT

This invention is made with government support under Grant Number GM60799/EB00264 awarded by the National Institutes of Health. The government may have certain rights in this invention.

BACKGROUND OF THE INVENTION

1. Field of the Invention

The present invention relates generally to mixing devices, and more particularly to a mixing device suited for a microfluidic environment.

2. Description of the Prior Art

Mixing fluids efficiently when the mixing volume is both temporally and spatially small poses problems. If the nature of the fluid changes upon mixing, for example, in terms of viscosity, flow dynamics are altered and the mixing efficiency is further lowered. An increase in viscosity delays the transition to turbulence, leading to lower mixing efficiencies, as the only mixing may occur by diffusion at the boundaries between the fluids.

There are several instances when it is desirable to achieve maximal mixing in a very short duration. Sub-optimal interaction of the fluids to be mixed leads to no or incomplete reaction. Mixing optimization in a microfluidic environment poses more problems because the volumes of the fluids involved are too small to use large conventional mixers. In addition to the chemical field, which involves small reactant volumes, the rapidly growing fields of drug discovery and modern biotechnology in general often encounter situations wherein bioefficacy testing or the effect of micro-volumes of molecules on cells, particles or other bioactive reagents have to be accurately studied. The difficulty of isolation and the cost of synthesis preclude testing of large volumes of compounds. Thus it becomes necessary to ensure that very small amounts of compounds are able to interact optimally so as to render accurate results.

Micromixing will be valuable for any application in biotechnology where small fluid volumes need to be mixed. In a confluence of two or more fluids at low volume, for example less than 1 microliter, and in dimensions of 100 micrometers, mixing primarily takes place by diffusion at their common boundaries. Consequently, mixing is very poor if the duration of the interaction is short. Also, if the flow is laminar, efficiency of mixing becomes even poorer (Beard, D. A., Taylor dispersion of a solute in a microfluidic channel, J. Applied Physics, 89: 4667-4669, 2001; Brody et al., Biotechnology at low Reynolds numbers, *Biophys. J.,* 71:3430-3441, 1996; Knight et al., Hydrodynamic focusing on a silicon chip: mixing nanoliters in microseconds, *Phys. Rev. Lett.* 80:3863-3866, 1998, the entire contents and disclosures of which are hereby incorporated by reference herein). It is well known that when viscosity of a fluid increases, diffusion decreases, contributing to poor mixing. Thus in situations where cells or particulate matter are added to a free-flowing fluid medium as in many bioanalytical systems, interactions of the constituents may be sub-optimal. In the micron size range, small Reynolds numbers govern the delivery of aqueous samples. As fluid transport systems get progressively smaller, viscous forces dominate over inertial forces, thus rendering turbulence nonexistent. This problem is acute in microfluidics (Ethers et al., Mixing in the offstream of a microchannel system, Chemical Engineering and Processing, 39:291-298, 2001). There are times when the reaction must take place in a sterile or aseptic environment without extraneous contaminants. At other times, the reaction may peak soon after the reactants come into contact and a read-out may not be possible or may become inaccurate, if delayed. Where the design limitations stipulate for sterility, a short mixing interval and a laminar-flow, in-flow mechanisms for bringing about effective mixing within the tube or channel become desirable and sometimes critical to effective means of measurement and analysis. Commonly used microfluidic mixers are diffusion-enhanced or highly complex and require a few seconds to achieve thorough mixing: They have not been able to address most of the above limitations effectively. Thus the need for in-flow mixing mechanisms for bringing about optimal mixing of a plurality of microfluids is still unmet.

SUMMARY OF THE INVENTION

It is therefore an object of the present invention to provide an efficient device for disrupting laminar flow within a flow-tube for efficient mixing of the constituents.

Another object of the present invention is to provide efficient mixing of multiple confluent microfluidic streams by disrupting laminar flow of these fluids.

It is yet another object of the present invention to enable efficient mixing of microvolumes of multiple samples.

According to the first broad aspect of the present invention, there is provided a method of mixing samples in-line in a microfluidic system, comprising: introducing a first fluid sample into a flow-tube at a first end at a first velocity via a first conduit; introducing a second fluid sample into the flow-tube at the first end at a second velocity, the second velocity different from the first velocity, via a second conduit, wherein the first fluid sample and the second fluid sample converge in the flow tube to form an interface; whereby the first fluid sample and the second fluid sample mix at the interface within the flow-tube, wherein fluid flow at the first end of the flow-tube is laminar and fluid flow at a second end of the flow-tube is laminar, and wherein the flow-tube has a constant diameter between the first end and the second end of the flow-tube.

According to the second broad aspect of the invention, there is provided a microfluidic apparatus for mixing samples in-line, comprising: means for introducing a first fluid sample into a flow-tube at a first end at a first velocity via a first conduit; means for introducing a second fluid sample into the flow-tube at the first end at a second velocity, the second velocity different from the first velocity, via a second conduit, wherein the first fluid sample and the second fluid sample converge in the flow tube to form an interface; whereby the first fluid sample and the second fluid sample mix at the interface within the flow-tube, wherein fluid flow at the first end of the flow-tube is laminar and fluid flow at a second end of the flow-tube is laminar, and wherein the flow-tube has a constant diameter between the first end and the second end of the flow-tube.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

Figure 1:
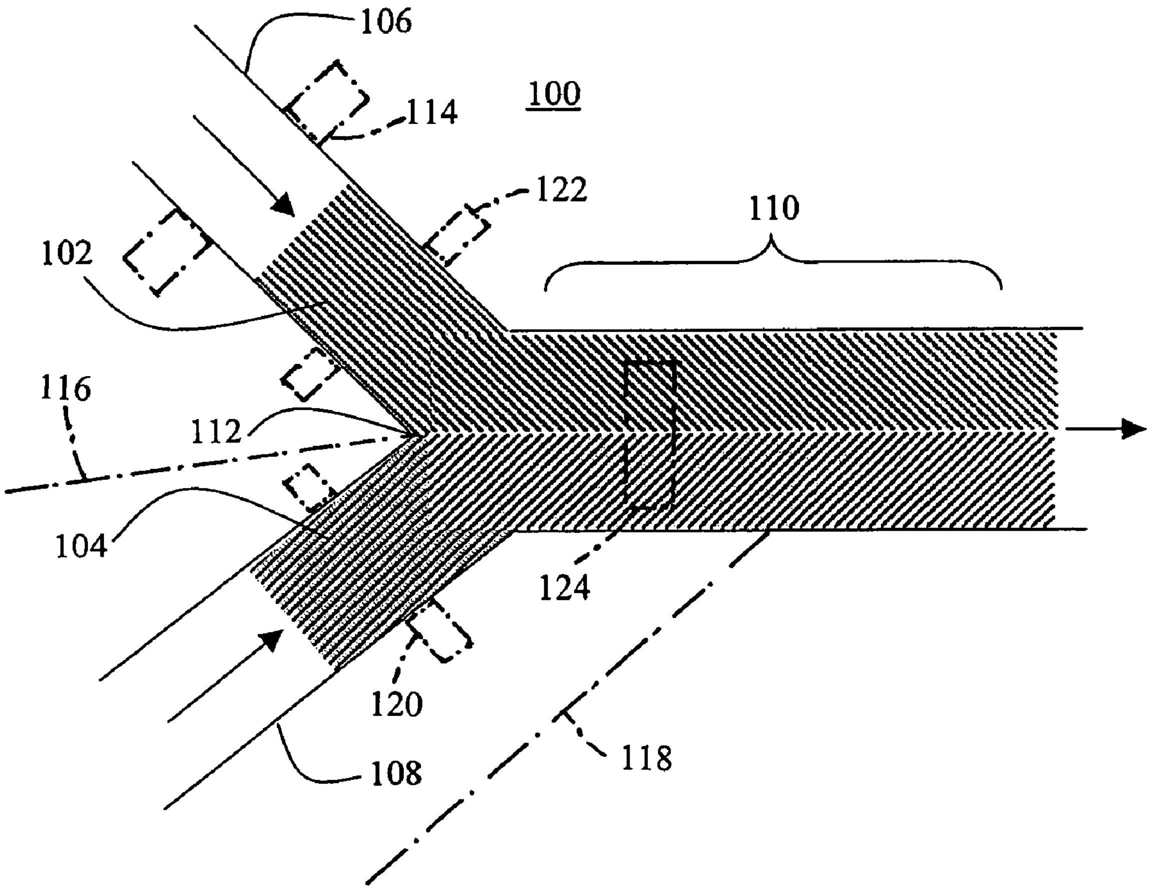
FIG. 1 illustrates in schematic form a mixing apparatus in accordance with an embodiment of the present invention.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "laminar flow" refers to substantially turbulence-free flow of multiple fluid streams into or through a flow-tube of a mixing apparatus from a plurality of receiving tubes feeding the flow-tube.

For the purposes of the present invention, the term "Poiseuille flow" refers to pressure-driven flow in a channel or circular conduit, characterized by a parabolic velocity profile.

For the purposes of the present invention, the term "Reynolds number (Re)" refers to the function $DU\rho/\nu$ used in fluid flow calculations to estimate whether flow through a pipe or conduit is streamline or turbulent in nature. D is the inside pipe diameter, U is the average velocity of flow, $\rho$ is density, and $\nu$ is the viscosity of the fluid. Reynolds number values much below 2100 correspond to laminar pipe flow, while values above 3000 correspond to turbulent flow. The range of Reynolds numbers in the micromixer is on the order of 1 to 100, well below the transition to turbulence.

For the purposes of the present invention, the term "Peclet number (Pe)" refers to the function $ud/\alpha$, where u is a characteristic flow velocity, d is a characteristic dimension and $\alpha$ is the diffusivity. A Peclet number describes the ratio of mass transfer by convection to that by diffusion.

For the purposes of the present invention, the term "flow-tube" refers to a containment vessel that receives reactants/analytes and cells/particles from one or a plurality of tubes at one end and conveys the mixed fluids into an analytical instrument or a receiving container at the second end. Flow-tubes of the present invention may be channels or other structures that funnel the fluid from one point to another, where the cross-sectional shape may preferably be circular, but may also be square, rectangular, elliptical, or any suitable variation thereof.

For the purposes of the present invention, the term "fluid flow stream" refers to a stream of fluid that is contained in a fluid flow path such as a tube, a channel, etc.

For the purposes of the present invention, the term "fluid flow path" refers to device such as a flow-tube, channel, etc. through which a fluid flow stream flows. A fluid flow path may be composed of several separate devices, such as a number of connected or joined pieces of tubing or a single piece of tubing, alone or in combination with channels or other different devices.

For the purposes of the present invention, the term "flow field" refers to the description of the velocity of a fluid particle at any given position.

For the purposes of the present invention, the term "slug" refers to a finite volume of liquid in a contained flow, separated from other slugs by gas bubbles.

For the purposes of the present invention, the term "interface" refers to the boundary between at least two fluids. In the present invention, the interface extends along the normal axis of fluid flow through a flow-tube.

Figure 4:
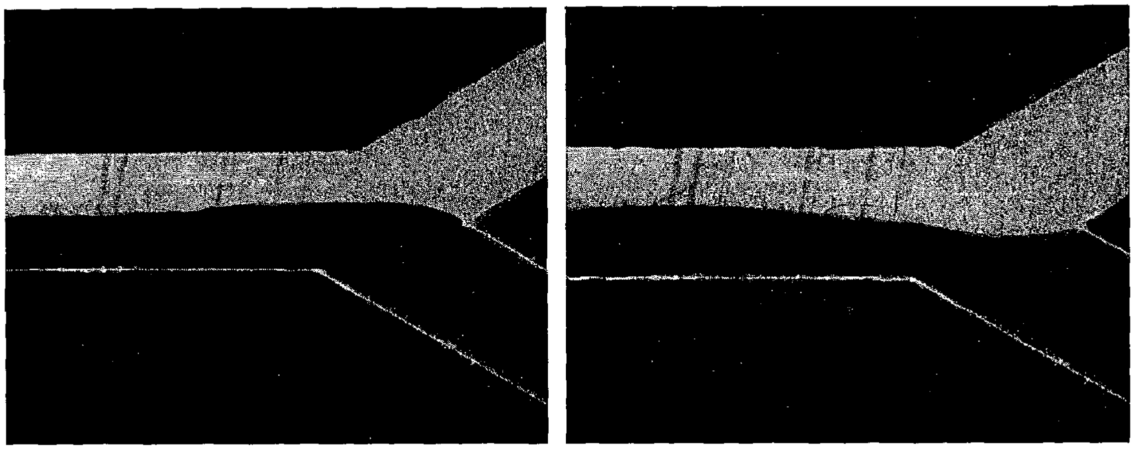
FIG. 4 shows cross-sectional images of a fluid flow stream showing two fluids mixing and a wavy interface forming at the fluid junction.

For the purposes of the present invention, the term "wavy interface" refers to an interface between at least two fluids in which the fluids undulate together. The amplitude of the waves of the wavy interface are dependent upon the velocities of the fluids, the densities of the fluids, and the dimensions of the tubing. See FIG. 4 for examples of a wavy interface.

For the purposes of the present invention, the term "plume" refers to a fluid dynamic in which at least two fluids are folded extensively around each other. See FIG. 7 for an example of a plume in a fluid flow.

For the purposes of the present invention, the term "disruption of laminar flow" refers to any turbulence or disruption caused in the laminarity of fluid flow in a flow tube.

For the purposes of the present invention, the term "pinch valve" refers to a valve that may be used to prevent or allow fluid to flow through a conduit or flow tube of the present invention.

For the purposes of the present invention, the term "normal axis of flow" refers to the general downstream flowing axis of a fluid within a flow-tube.

For the purposes of the present invention, the term "intermittently" refers to any regular or irregular periodic application.

For the purposes of the present invention, the term "non-reactive" refers to a substance that is not involved in any appreciable or effective reaction with another substance.

For the purposes of the present invention, the term "reactive materials" refers to any reactant that may be utilized in a mixing and analyzing system of the present invention.

For the purposes of the present invention, the term "microfluidic" refers to fluid flow phenomena pertinent to characteristic flow scales on the order of 1-1000 microns.

For the purposes of the present invention, the term "driven cavity" refers to the process where contents of two sample lines are mixed in a mixer, using a driving force to cause mixing of samples.

For the purposes of the present invention, the term "pulsatile fluid motion" refers to the motion that is created in a fluid as a result of being driven by a peristaltic pump.

For the purposes of the present invention, the term "pulsatile fluid mixing" refers to the process where contents of two sample lines are mixed in a mixer, using the pulsatile fluid motion associated with a discrete or discontinuous sample unit to mix the discrete or discontinuous sample unit with a continuously drawn or provided material. The pulsatile fluid motion forces the fluid in the discrete or discontinuous sample to mix with the continuously supplied material due to the different velocities of the samples. Thus, the driving force behind mixing is the pulsatile fluid motion.

For the purposes of the present invention, the term "diameter" refers to the characteristic cross sectional inner dimension of a device through which a fluid flows such as a flow-tube, channel, pore, etc.

For the purposes of the present invention, the term "micro-channels" refers to channels having a diameter of ~0.01 inch=0.0254 cm.

For the purposes of the present invention, the term "discontinuous sample" refers to discrete sample units preceded and followed by air bubbles.

For the purposes of the present invention, the term "particles" refers to any particles such as beads or cells that may be detected using a flow cytometry apparatus, whether in solution or suspension, etc. The particles to be analyzed in a sample may be tagged, such as with a fluorescent tag. The particles to be analyzed may also be bound to a bead, a cell, a receptor, or other useful protein or polypeptide, or may just be present as free particles, such as particles found naturally in a cell lysate, purified particles from a cell lysate, particles from a tissue culture, etc. When the particles to be analyzed are biomaterials, drugs may be added to the reagent samples to cause a reaction or response in the particles with which the reagent samples are mixed.

For the purposes of the present invention, the term "drug" refers to any type of substance that is commonly considered a drug. For the purposes of the present invention, a drug may be a substance that acts on the central nervous system of an individual, e.g. a narcotic, hallucinogen, barbiturate, or a psychotropic drug. For the purposes of the present invention, a drug may also be a substance that kills or inactivates disease-causing infectious organisms. In addition, for the purposes of the present invention, a drug may be a substance that affects the activity of a specific cell, bodily organ or function. A drug may be an organic or inorganic chemical, a biomaterial, etc. The term drug also refers to any molecule that is being tested as a potential precursor of a drug.

For the purposes of the present invention, the term "plurality" refers to two or more of anything, such as a plurality of samples.

For the purposes of the present invention, the term "homogeneous" refers to a plurality of identical samples. The term "homogeneous" also refers to a plurality of samples that are indistinguishable with respect to a particular property being measured by an apparatus or a method of the present invention.

For the purposes of the present invention, the term "heterogeneous" refers to a plurality of samples in a fluid flow stream in which there are at least two different types of reagent samples in the fluid flow stream. One way a heterogeneous plurality of samples in a fluid flow stream of the present invention may be obtained is by intaking different reagent samples from different source wells in a well plate.

Description

The present invention provides for mixing of small volumes of fluids at relatively low flow rates, i.e. low Reynolds numbers. The present invention may be useful in the field of drug discovery by utilizing high throughput flow cytometry or may be useful in any other application where the mixing of microliter sample volumes is required. The capability of the present invention to provide effective mixing of small volumes of fluid allows throughputs to increase significantly compared to current capabilities.

Mixing of different, miscible phases typically results from interfacial diffusion. The type of mixing that is commonly observed (for example, smoke in the atmosphere, or milk in coffee) is strongly aided by turbulence, which acts to quickly stretch and fold the interface between the different phases, thereby reducing the diffusion distance. At low Reynolds numbers, turbulence is minimal or even absent, and therefore other mechanisms to stretch and fold interfaces must be devised.

In the present invention, a flow field is used to amplify interface disturbances generated by the pulsatile pumping action of a peristaltic pump within a slug of fluid consisting of two reagents. The reagents must be well-mixed in order for a full reaction to occur. Mixing occurs naturally by diffusion, but this can be aided by reducing the diffusion length. The length to diameter ratio (L/D) of the slug is variable. Poiseuille conditions exist in the parts of the slug away from the leading or trailing end. If the slug is entirely contained within a section of the tube, a recirculating flow occurs where fluid at the leading end is recirculated to the trailing edge. Longer L/D ratios allow more interface distortion within a slug, hence improving mixing, but result in less efficient recirculation, leading to reduced mixing. Optimal L/D ratios depend on several parameters, including the frequency of the interface distortion, a function of the particular pump and tubing used. Additional interface distortion may be created by placing obstacles in the flow, by utilizing density gradients or by externally applied body forces, such as a magnetic force applied to ferromagnetic suspended particles.

As shown in FIG. 1, fluids 102 and 104 are introduced into flow tube 110 by branches 106 and 108 of Y shaped conduit 100, where each fluid 102 and 104 is introduced through one of the upper branches 106 and 108 of the Y. In FIG. 1, fluids 102 and 104 are introduced at a constant flow rate and thus no noticeable mixing occurs at junction 112 of fluids 102 and 104. The interface between fluids 102 and 104 beginning at junction 112 extends down the normal axis of fluid flow between fluids 102 and 104, and little to no mixing is present.

Figure 2:
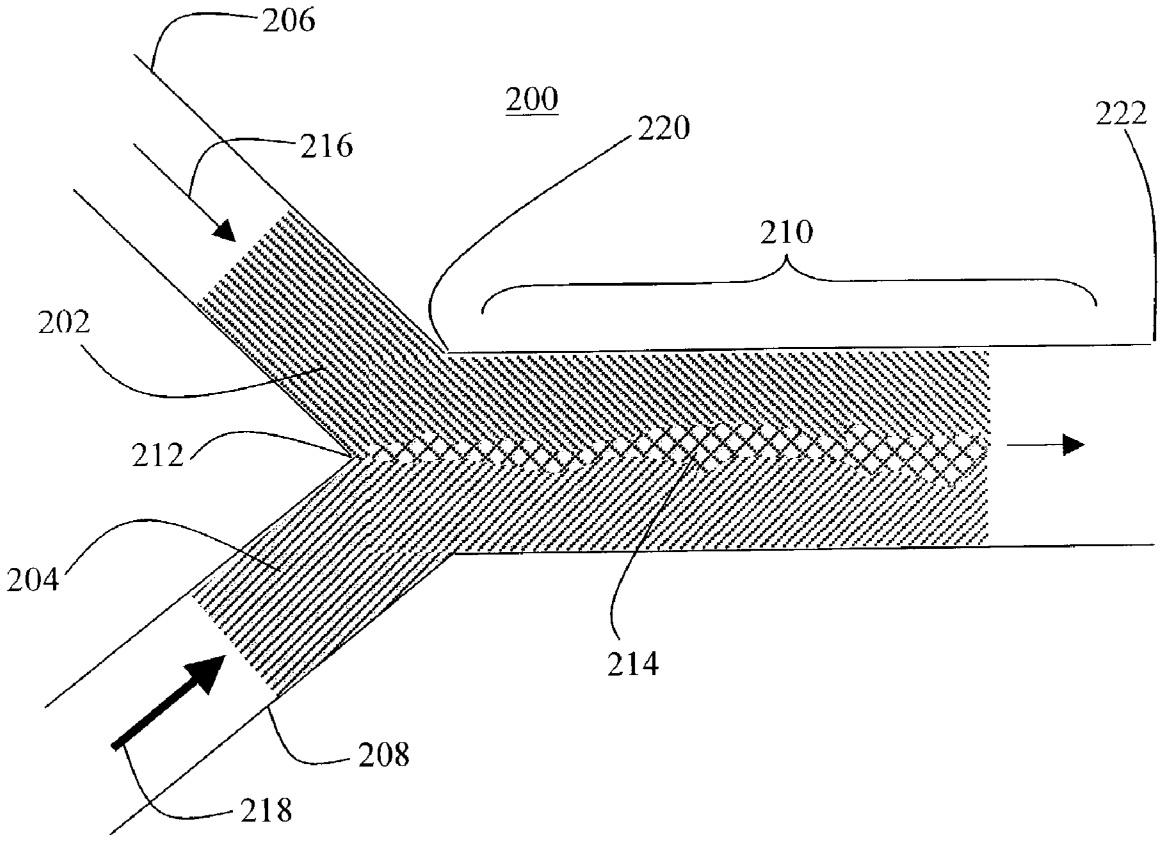
FIG. 2 illustrates in schematic form a mixing apparatus in accordance with an embodiment of the present invention.

As shown in FIG. 2, fluids 202 and 204 are introduced into flow tube 210 by a Y shaped conduit 200, where each fluid 202 and 204 is introduced through one of the upper branches 206 and 208 of the Y. In FIG. 2, fluids 202 and 204 are introduced at flow rates that vary over time and thus mixing occurs at junction 212 of fluids 202 and 204 and extends along the interface between fluids 202 and 204. Mixing region 214 illustrates mixing of fluids 202 and 204 as fluids 202 and 204 flow through flow tube 210. By varying the force component 216 and 218 applied to propel fluids 202 and 204, respectively, along conduit 200, the amplitude of mixing may be controlled. Flow tube 210 may be defined to have a first end 220 and a second end 222. First end 220 may be defined as the beginning of a region of constant diameter of flow tube 210. Second end 222 may be defined as a point downstream of first end 220 between which the diameter of flow tube 210 is constant. Mixing may occur only partly or completely between first end 220 and second end 222. Further mixing may occur downstream of second end 222 through various mechanisms. In addition, a flow cytometer or other suitable analysis device (not shown) may be used to measure the mixed fluids.

Suitable mechanisms of the present invention for providing the force to propel fluids through a flow tube include peristaltic pumps 114 (FIG. 1), syringes, air pressure, electromagnetic devices.

Suitable tubing dimensions range from ten(s) to hundreds of microns in diameter.

Although only a Y junction is represented in FIGS. 1 and 2, it should be appreciated by one of ordinary skill in the art that any suitable mixing apparatus arrangement may be used. Suitable mixing apparatus arrangements may have more than two input tubes or branches and may be at any location along a flow-tube. More than two fluids may be mixed together using various mixing apparatus arrangements. As depicted in FIG. 1. a third conduit or input tube 116 may extend to a first or upstream end of flow tube 110. Alternatively, a third conduit or input tube 118 may extend to flow tube 110 at a point between the first or upstream end and a second end of the flow tube.

Pulsatile action is important to the function of the present invention. The velocity due to the pulsation is preferably significantly larger than the mean flow velocity. The pulsation may preferably be staggered by a delay, which is small compared to the pulsation period. Details of the timing parameters may be found in Truesdell, R. A., "Laminar Mixing Induced by Unsteady Flow", Master's thesis, University of New Mexico, 2002, the entire contents and disclosure of which is hereby incorporated by reference.

The amplitude of the waves generated by the pulsed flow of the input fluids is directly related to the maximum amount of mixing that occurs, since folding and interface stretching take place in the volume of fluid contained between the wave crests and troughs. A lower quality peristaltic pump may perform better than a high-quality 10-roller pump in some situations. Increasing the diameter of the tubing that runs through the pump head results in increased pulsation amplitude. However, the pump speed is preferably adjusted to compensate for the increased pumping volume, thus producing longer waves, which may be detrimental to mixing. In general, reliance on the type of pump and tubing to encourage mixing is undesirable.

To better control and enhance the mixing effect provided by the pulsed flow inherent in peristaltic pumping action, pinch valves 120 and 122 may be introduced just prior to each branch of the Y-connection, or other suitable connection. The pinch valves 120 and 122 operate in a manner similar to the peristaltic action in that they compress the tube just as the peristaltic pump does. The effect is twofold. First, during compression of the tube, a certain amount of positive pumping action is created, while negative pumping action is created upon release. Second, the mean flow of the pinched stream is interrupted for the duration of the valve actuation.

In contrast to the peristaltic pumping action, which is primarily intended to provide a mean flow rate, the action of the pinch valves 120 and 122 may be controlled independently. The parameters that may be controlled are the pulse width (the amount of time that the valve is closed), the period (time between pulses), and the delay between the pulses for each incoming stream. As with the peristaltic pumping action, in phase pulses in theory would not produce any interface distortion.

Further disruption of fluid flow in the methods and apparatus of the present invention may be generated by incorporation of complex-shaped obstacles in the flow, such as micromixers 124 (FIG. 1), whether magnetic or not, or other suitable obstructions.

In addition, varying density gradients may be used to affect the mixing of two or more samples. The density difference required is a function of the viscosity of the fluid. For aqueous solutions a density difference of 1% is sufficient to generate significant interface distortion.

Also, increased mixing may be generated by magnetically activated suspended particles. Small spheres held in place and oscillated by a magnetic field can also serve to induce mixing, due to the disturbance in the velocity field around the particles that extend for several particle radii. The size of the particles is preferably on the order of 1/10 to 1/5 of the tube diameter.

The present invention describes a low-Reynolds number mixing flow driven through a Y connection by peristaltic pumping. Peristaltic pumps are commonly used in chemical and biological applications because contact of the working fluid with moving parts is eliminated and because of the simplicity of their operation. Flow visualization of two pump-driven mixing streams reveals the unsteadiness of the flow resulting in limited interface distortion, which is amplified by the Poiseuille flow, leading to increased diffusion. Preferably, the pulsations in the incoming streams are in antiphase to maximize the interface distortion. However, mixing solely due to peristaltic pumping is shown to be incomplete in some situations, and the oscillatory parameters of the flow are largely predetermined by the choice of the peristaltic pump.

The addition of pinch valves controlled by a timing device to the experimental setup makes it possible to generate a region of disordered flow where large-scale interface distortion occurs. The residence time of fluid in the disordered region is constrained by the mean flow. The limit case of zero mean flow is characterized by the length of the mixing interface between the two streams in the Y connection growing consistently with exponential law, which suggests that the flow due to the action of the pinch valves is chaotic. An increase in the frequency of operation of the pinch valves leads to increased stretching and folding of the interface, and hence improved mixing. In the cases of improved mixing, the mixing interface appears to acquire fractal properties, while poorly mixing cases are characterized by near-trivial interfacial fractal dimension. Within the period of operation of the valves, the interface distortion may be maximized by controlling the length of time each valve is closed, and the delay between these.

The present application may have direct application in high throughput flow cytometry and other areas where continuous mixing of reagents at low Re is needed (for example food, chemical, printing, biodetection). Because the mixer of the present invention is effective at low Re, it is particularly suited to microscale applications. In applications where particle-laden fluids are transported, moving or stationary obstacles in the flow may be undesirable. These applications are most likely to benefit from low-Re mixing enhancement techniques described in the present invention.

EXAMPLE I

Figure 3:
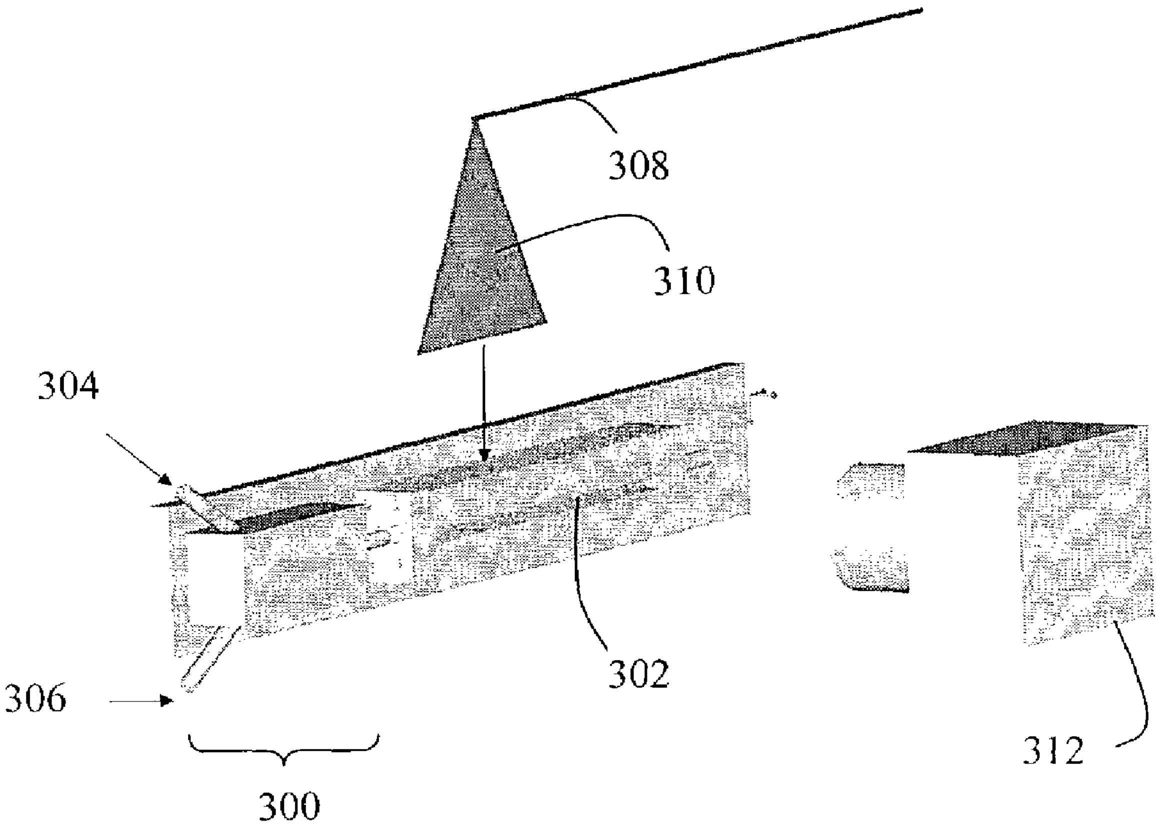
FIG. 3 illustrates in schematic form a mixing and analysis apparatus in accordance with an embodiment of the present invention.

A "Y" conduit 300 and an 8" long mixing channel 302 were constructed out of Polymethylmethacrylate (PMMA), as shown in FIG. 3. A zinc-chloride/water mixture was prepared so as to match the index of refraction of the PMMA (1.49). The mixture was used as the working fluid fed through each branch 304 and 306 of "Y" conduit 300, thus allowing flow visualization of any cross-section of the flow. A laser beam 308 was passed through a cylindrical lens (not shown) to form a sheet 310, which was used to illuminate the cross-section of interest in the flow. One of the fluids was seeded with a very small amount of tracer, namely sub-micron sized $TiO_2$ particles. One side of "Y" conduit 300 was hooked up to a peristaltic pump (not shown) while the other side was hooked up to a syringe pump (not shown). The peristaltic pump provides time periodic (intermittent) flow. A camera 312 was mounted so as to view the cross-section of the flow illuminated by laser sheet 310.

Images were taken with camera 312 (1536×1024 pixel greyscale digital camera) at various stages of mixing in various sections of mixing channel 302. FIGS. 4A and 4B are cross-sectional images of a fluid flow stream showing two fluids mixing and a wavy interface forming at the fluid junction. Light scattered by tracer particles leads to increased brightness in the illuminated section of the flow corresponding to the seeded fluid. The images show that the seeded and unseeded fluids are merging at the Y connection. FIGS. 4A and 4B show that a wavy boundary is being formed. The Poiseuille flow results in amplification of the initial wavy disturbance.

Figure 5:
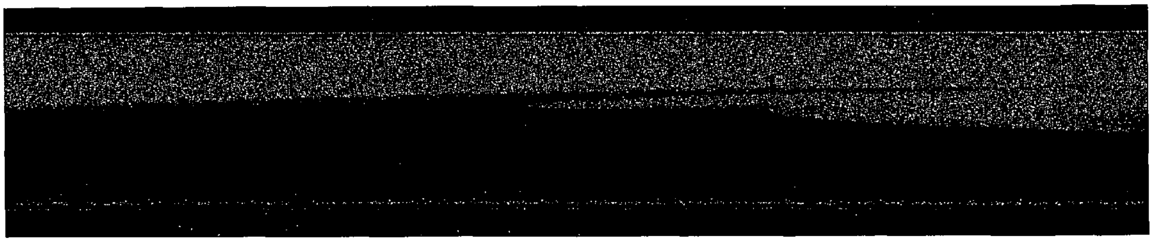
FIG. 5 is a cross-sectional image of a fluid flow stream showing two fluids mixing and initial folding of a wavy interface at the fluid junction.

FIG. 5 is a cross-sectional image of a fluid flow stream showing two fluids mixing and initial folding of a wavy interface at the fluid junction. The image shows the first fold that is forming between the two fluids. This fold increases the interfacial area between the two fluids and thus allows more diffusive mixing to take place.

Figure 6:
FIG. 6 is a cross-sectional image of a fluid flow stream showing two fluids mixing and folding of a wavy interface at the fluid junction.

FIG. 6 is a cross-sectional image of a fluid flow stream showing two fluids mixing and folding of a wavy interface at the fluid junction. The image shows the flow further downstream in the fluid flow stream as compared to that shown in FIG. 5. FIG. 6 shows that more and more folding has occurred thus increasing the interfacial area between the two fluids.

EXAMPLE II

Figure 7:
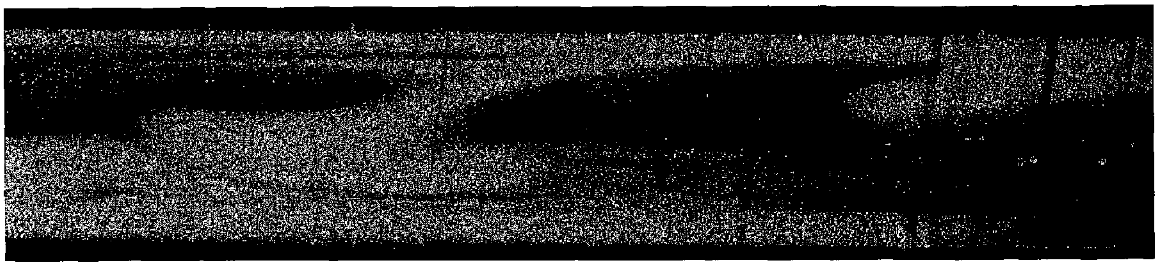
FIG. 7 is a cross-sectional image of a fluid flow stream showing two fluids mixing and interface distortion at the fluid junction.

An experiment performed with slight density mismatch (approximately 1%) between the seeded and unseeded fluids shows significant interface distortion due to the formation of a plume, as shown in FIG. 7. This plume effect may be exploited, for example by heating and subsequent cooling of the flowing fluid at various locations along the mixing channel to alter the fluid densities. This may be effected by wrapping two tubes, carrying hot and cold fluid respectively, around the main tube in a helical arrangement, resulting in alternating hot and cold zones generating density differences in the flowing fluid.

A quantitative study, see Truesdell, R. A., "Laminar Mixing Induced by Unsteady Flow", Master's thesis, University of New Mexico, 2002, the entire contents and disclosure of which is hereby incorporated by reference, shows that close to 100% mixing can be achieved in short distances by applying the pulsatile mixing described above.

EXAMPLE III

An experimental setup according to the present invention may utilize a flow cytometer, for example, with tubing of diameter $2.5\times10^{-4}$ m and a total flow rate of $3.333\times10^{-9}$ $m^3s^{-1}$ (200 μl per minute) corresponding to a velocity at each inlet of 0.03395 $ms^{-1}$. With water as the working fluid ($\nu=1.14\times10^{-6} m^2s^{-1}$), the Reynolds number at the outlet of the Y is approximately 15, well within the laminar flow regime. To simplify the experiment, the limit of no diffusion (Pe>>1) and low Reynolds number (Re<<1) is investigated here. This represents the worst-case scenario, and the presence of diffusion can only be beneficial to mixing.

The diameter of the tubing in the scaled up model is 0.003175 m. Using a 1536×1024 pixel camera with a Sigma 105 mm macro lens and a series of close-up filters to reduce the focal length, it is possible to obtain sufficiently detailed digital images of the flow, with approximately 250 pixels per diameter length. The resultant image would thus contain a section of tube of approximately six diameter lengths. With a flow rate of $42\times10^{-10}$ $m^3s^{-1}$, the Re for the scaled-up model is approximately 0.31.

Refractive index matching between the mixer model and the fluid provides undistorted imaging of the flow inside the model. The model consists of a Y-connection, followed by a long straight tube. The diameter of the arms of the Y and of the long tube are equal. The Y section is machined from a small block of PMMA (refractive index 1.488). Because drilling a long (approximately 500 diameter lengths) circular channel is impractical, an extruded PMMA tube is placed in a channel milled in a long rectangular PMMA block. The gap between the tube and the block is filled with refractive index matched fluid and a thin PMMA sheet is glued to the top of the block to contain the fluid.

A solution of Zinc Chloride ($ZnCl_2$) and de-ionized water is used as the working fluid. The refractive index of the solution can be adjusted by changing the amount of $ZnCl_2$ per unit mass of water. A mass ratio of 1.97 parts $ZnCl_2$ to 1 part water results in the correct refractive index, measured using a Mettler-Toledo DR-50 refractometer at 22° C. The rheological properties of the fluid were characterized using a Stresstech rheometer. The fluid is Newtonian, with a viscosity of approximately 0.02 Pas at 22° C.

Because everything used in the apparatus including the working fluid has the same refractive index, light travels practically undetected within any cross-section. Cross-sections of interest are illuminated by a $<1\times10^{-4}$ m thick pulsed light sheet obtained by passing a laser beam through a cylindrical and a spherical lens. The laser beam is generated by a New Wave Research Gemini PIV Nd:YAG laser, with a pulse duration of 3-5 ns and power of about 20 mJ per pulse. The camera (Kodak Megaplus 1.6i) focused on the laser sheet is mounted above the viewing apparatus.

The camera and laser are stationary while the viewing apparatus is mounted on a traversing mechanism, allowing certain features of the flow to be followed if so required. The traversing mechanism is a computer controlled belt driven system. The servo motor is connected to a planetary inline gearhead with a 25:1 ratio. The system has a unidirectional repeatability of ±0.004 mm, an accuracy range of 0.020 mm to 0.162 mm, and a backlash range of 0.02 mm to 0.04 mm.

A Gilson Minipuls 3 peristaltic pump with ten rollers drives the fluids. The interface distortion produced by the peristaltic pumping action is thought to be responsible for the observed mixing of the incoming streams. The amplitude of the interface distortion may be controlled by changing the phase between pulsations in the incoming flows, which in turn is a function of the difference in the lengths of the tubes between the pump head and the mixer inlet. Equal lengths, corresponding to in-phase flow, do not produce interface distortion, while a difference in length equal to half the distance between adjacent rollers maximizes interface distortion.

Increased interface distortion may be obtained by interrupting the flow of either incoming stream by means of pinch valves. Two Neptune Research pinch valves are mounted just upstream of each branch of the Y. They are powered by a 12V power supply and controlled by two pulse generators. The period and pulse width of one valve are controlled by a master pulse generator. The second valve is controlled by a slave pulse generator, triggered by the first pulse generator with a controlled delay. The period and pulse width of the slave pulse may be controlled independently, however both are set to the same value as the master pulse to maintain an equal flow rate for both streams. Both pinch valves are normally open. An oscilloscope is used to monitor the valve operation.

One of the streams is seeded with small (approximately 0.2 μm) titanium dioxide ($TiO_2$) particles. These particles are very efficient Mie scatterers. Their density is higher than that of the working fluid, but they are sufficiently small to follow the flow without any noticeable settling on the time scale of the experiment. Illumination of the flow by the laser results in a 'light' stream (seeded) and a 'dark' stream (unseeded). The tracer amount used is small enough that there is no appreciable change in the density of the fluid. The mixture is approximately 1 part $TiO_2$ per 100,000 parts of the $ZnCl_2$/water solution. The laser pulses are triggered by the camera shutter. Only one laser pulse per image is used. The digital images are acquired via a Bitflow Roadrunner board, and stored on disk for subsequent post-processing. The average pixel intensities associated with the 'light' and 'dark' streams are subsequently employed to calibrate the images in terms of concentration of the 'light' stream material. The average intensity of 'dark' pixels corresponds to 0% concentration, the corresponding 'light' intensity is 100%. The intensity-concentration mapping is effectively linear because the light sheet illuminates a thin section of the flow, and the particle-seeding density is low.

EXAMPLE IV

Figure 8:
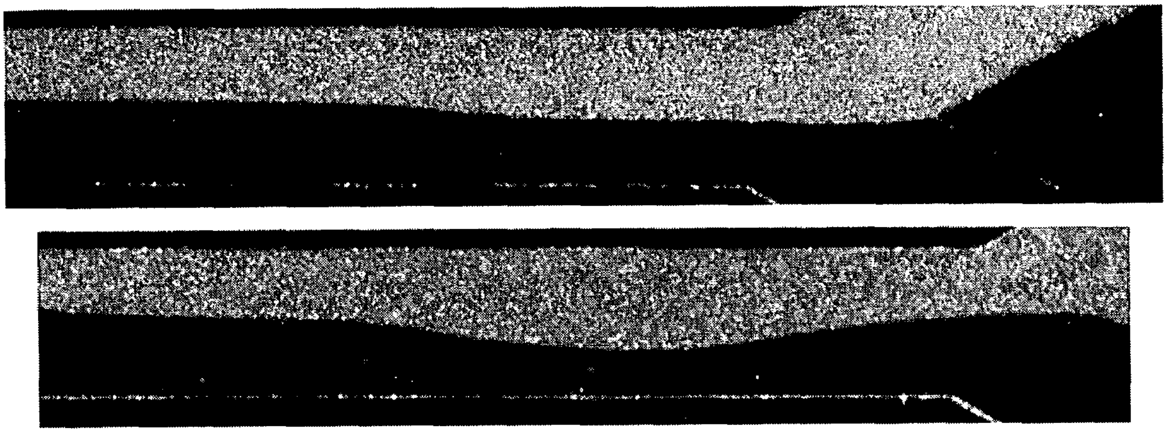
FIG. 8 shows interfaces generated by slightly out of phase flow (top) and fully out of phase flow (bottom)

In the present example, experiments were performed that visualized the effects of peristaltic action on the flow patterns at and after a Y-junction. Both incoming streams are driven by the same peristaltic pump. In FIG. 8, interfaces produced by pulsation are shown slightly out of phase (top) and 180° out of phase (bottom). The phase delay was produced by variation of the length of one of the tubes connecting the peristaltic pump to the apparatus.

Figure 9:
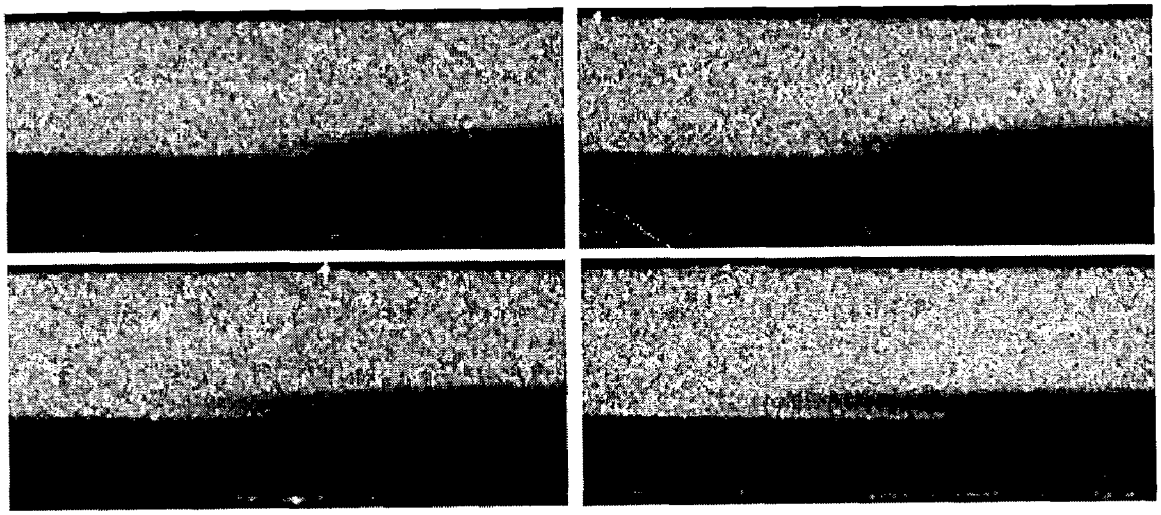
FIG. 9 is a sequence of images showing the first fold occurring after a Y-junction for slightly out of phase flow with the order of images being top left, top right, bottom left and then bottom right.
Figure 10:
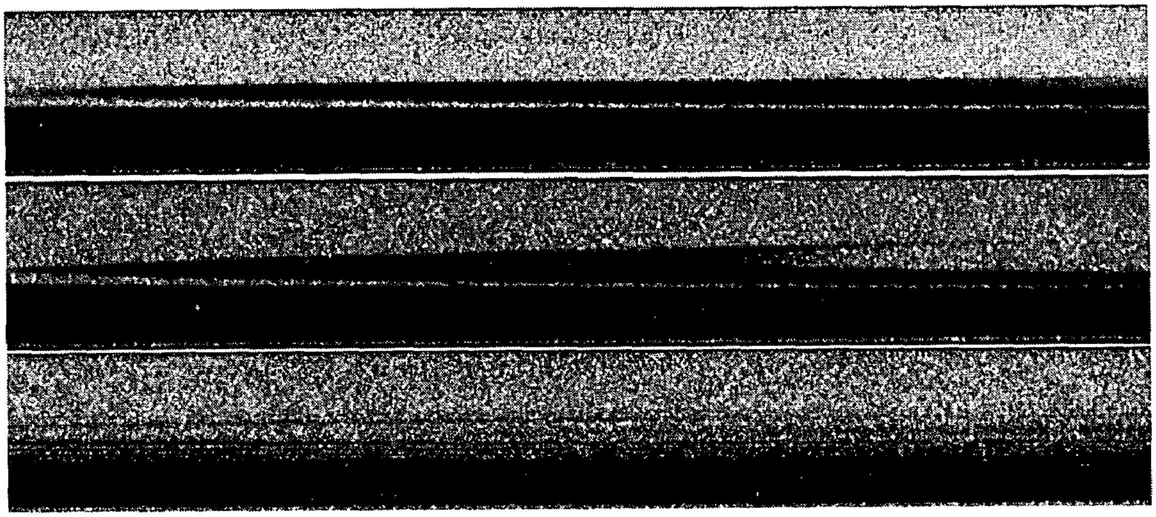
FIG. 10 shows folds at 82 diameter lengths downstream of a Y-junction for slightly out of phase flow (top), at 62 diameter lengths for out of phase flow (center) and at 162 diameter lengths for out of phase flow (bottom)

The formation of a wavy interface eventually leads to folding due to the flow profile. The traversing mechanism was used to follow an individual wave along the tube. FIG. 9 shows the formation of a fold. The formation of folds coincides with interface stretching, which promotes diffusion due to the larger interface area. Because of the parabolic mean velocity profile, waves with larger amplitude (out of phase flow) produce faster and more extensive folding. This difference is highlighted in FIG. 10.

At about 82 diameter lengths downstream from the Y, there is only one long fold for the slightly out of phase flow. For the fully out of phase flow, there is evidence of two folds at about 62 diameter lengths. Further down the viewing apparatus, at 162 diameter lengths, there is evidence of many folds and the center of the tube is beginning to appear mixed. Clearly, some mixing at the center of the stream is obtained, essentially with no cost, simply due to the peristaltic pumping action. However, this experiment shows that, if this effect is to be exploited fully, the pulsation of the streams should be 180° out of phase.

EXAMPLE V

Three sets of experiments were performed to explore the effect of using pinch valves according to the present invention. The parameters that may be controlled are the pulse width (the amount of time that the valve is closed), the period (time between pulses), and the delay between the pulses for each incoming stream. The three parameters above are non-dimensionalized by the time required for a particle at the center of the flow to move one diameter length. For these sets of experiments that time is 2.837 seconds. The first set of experiments is done using a period of approximately 0.493, the second set using a period of approximately 0.282, and the third using a period of approximately 0.141. Within each of these sets, the pulse width and delay are altered. Table I lists a subset of representative experiments performed and the relative non-dimensional parameters.

TABLE I

Non-dimensionalized pinch valve parameters.

| Experiment Number | Period | Pulse Width | Delay |
|---|---|---|---|
| Experiment 1 | 0.493 | 0.169 | 0.187 |
| Experiment 2 | 0.493 | 0.044 | 0.021 |
| Experiment 3 | 0.282 | 0.139 | 0.134 |
| Experiment 4 | 0.282 | 0.037 | 0.035 |
| Experiment 5 | 0.141 | 0.070 | 0.067 |
| Experiment 6 | 0.141 | 0.018 | 0.018 |

Figure 11:
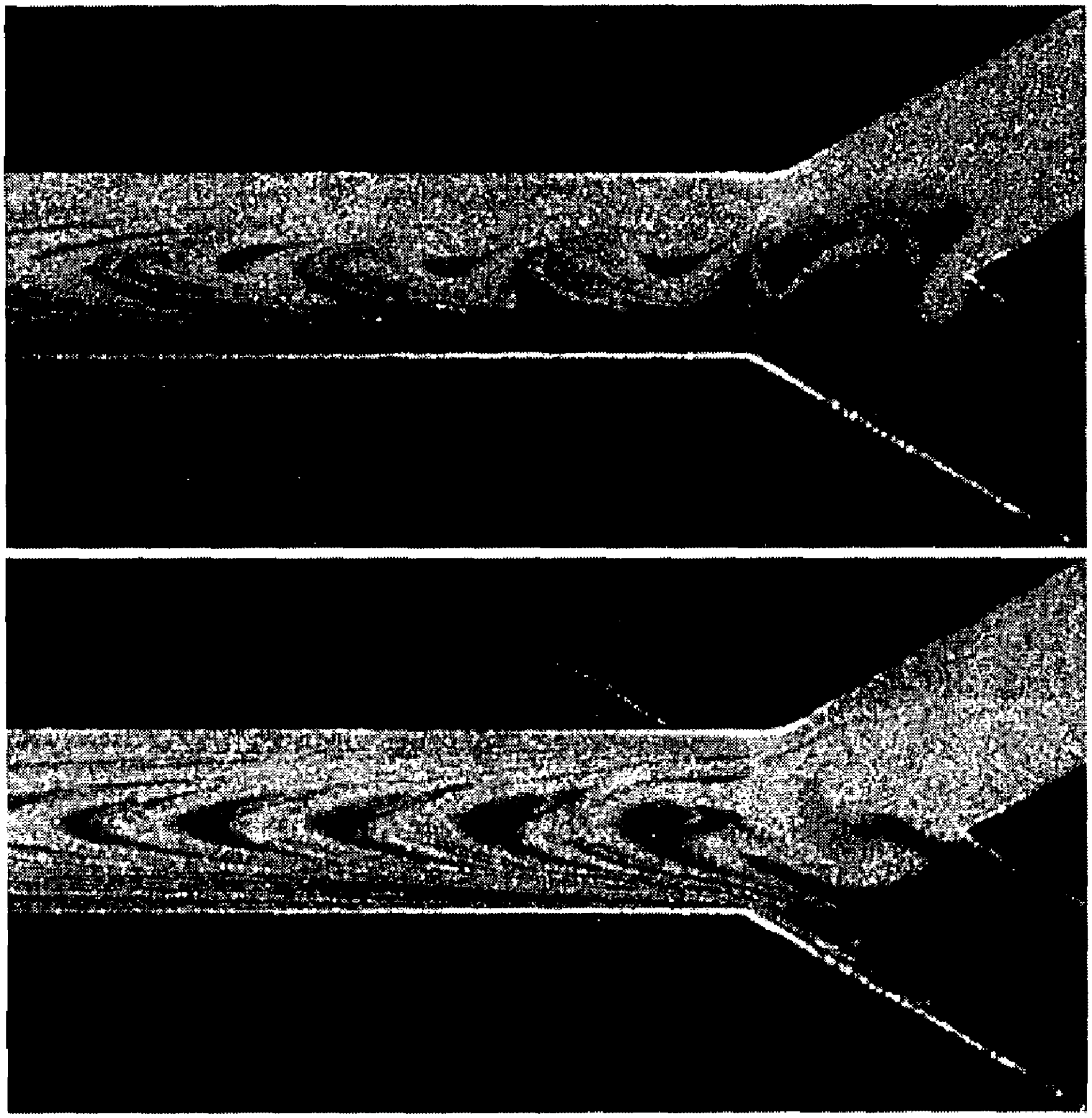
FIG. 11 shows the mixing involved with pinch valve experiments 1 (top) and 2 (bottom) from Table I.

The steady-state interface configuration in the vicinity of the Y-connection with a period of 0.493, and variations of the pulse width and delay (experiments 1 and 2), is shown in FIG. 11. Mixing is enhanced by a reduction of the pulse width and delay. With the larger pulse width, the interface does not span the entire width of the tube. The situation is improved by reducing the pulse width and the delay.

Figure 12:
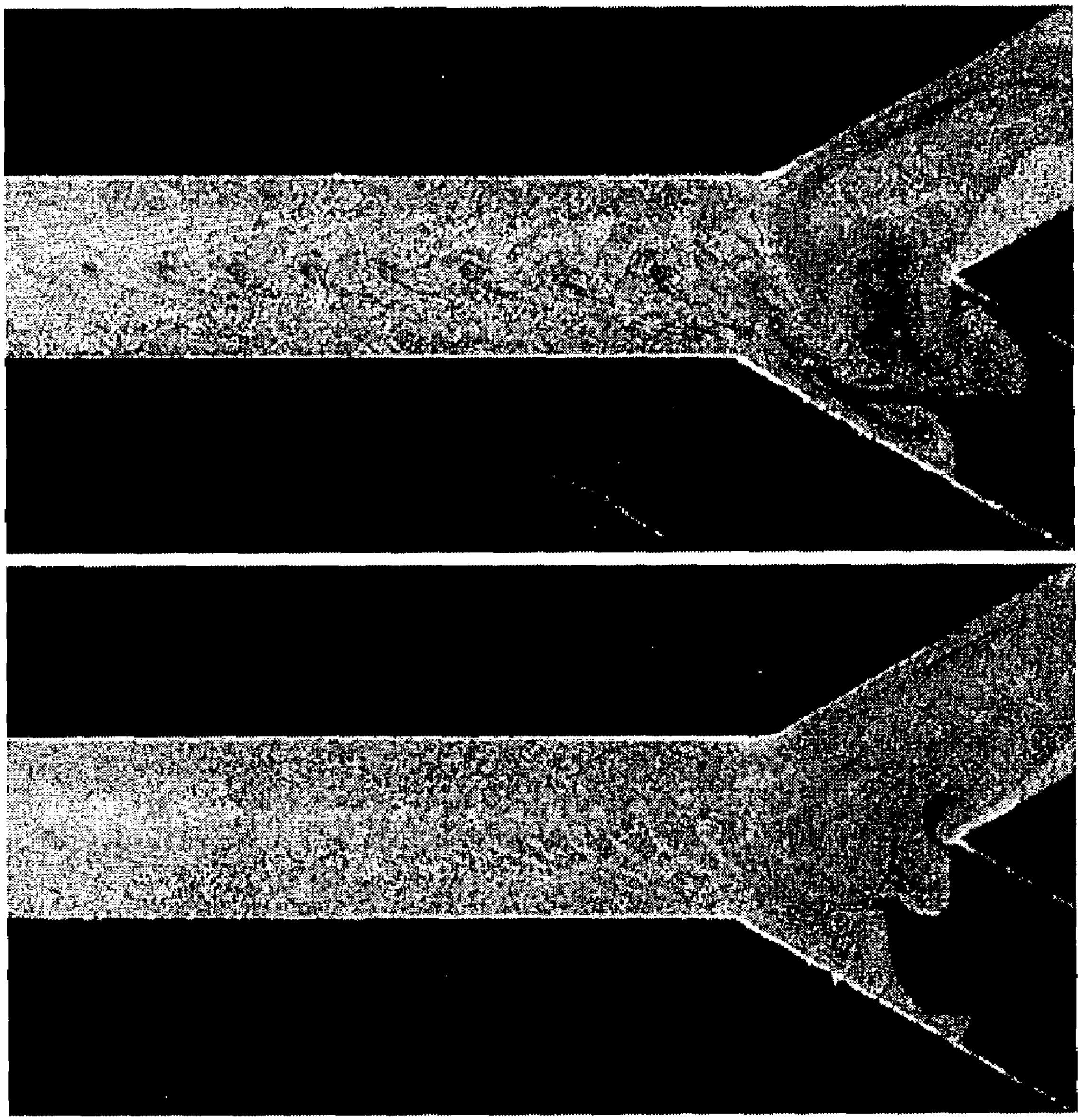
FIG. 12 shows the mixing involved with pinch valve experiments 4 (top) and 6 (bottom) from Table I.

Reduction of the period further improves mixing. The trend observed in experiments 1 and 2, namely that a reduction of the pulse width promotes mixing, is evident throughout the experiments, as can be observed in FIG. 12.

In general, mixing improves with a reduction in period, pulse width and delay. However, clearly a zero delay would not produce a distorted interface. Also, there are qualitative differences between the various experiments: for example, the mixing in experiment 4 is very good, but there remain some small, unmixed islands. These disappear in experiment 6, which appears to generate complete mixing.

Although the flow retains some periodicity, it appears that a small region of chaotic flow exists at the intersection of the three tubes, superimposed on a mean flow. The relative amount of time that a fluid volume spends in this apparently chaotic region determines the quality of mixing.

Figure 13:
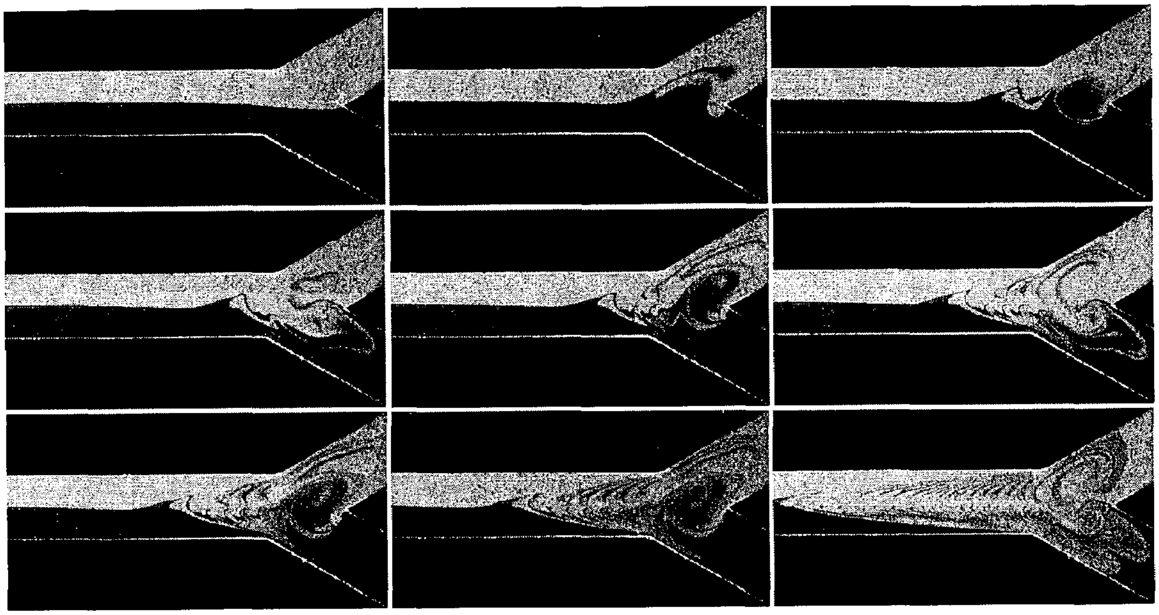
FIG. 13 shows transient flow upon startup of a mixing apparatus of the present invention for the parameters described in pinch valve experiment 5 from Table I, with the non-dimensionalized times being 0.0, 0.110, 0.242, 0.352, 0.451, 0.688, 0.787, 1.063, and 2.528 (read from top left across from left to right to bottom right)

The nature of the flow in the intersection region is best visualized by inspection of the transient flow following the onset of the pinch valve action for experiment 5, shown in FIG. 13. The interface appears to move from one arm of the Y to the other, and in the process folds over itself, eventually creating striations that are convected downstream by the mean flow. The dominant interface distortion mechanism appears to be the pulsation created by the rapid closure of the pinch valve, rather than the interruption of the flow. There are two possible routes for the fluid transported by the velocity pulsation due to valve shutoff: towards the base of the Y, or into the other branch. The latter path promotes further interface stretching and folding. Flow from one branch of the Y into the other is favored if a valve closure in one branch is preceded by a release in the other arm, explaining the improvement of mixing resulting from a reduction in the delay duration. Although the flow is driven by periodic action, the visualized tracer pattern at the Y does not repeat exactly. This is an indication that the flow indeed may be chaotic.

Figure 14:
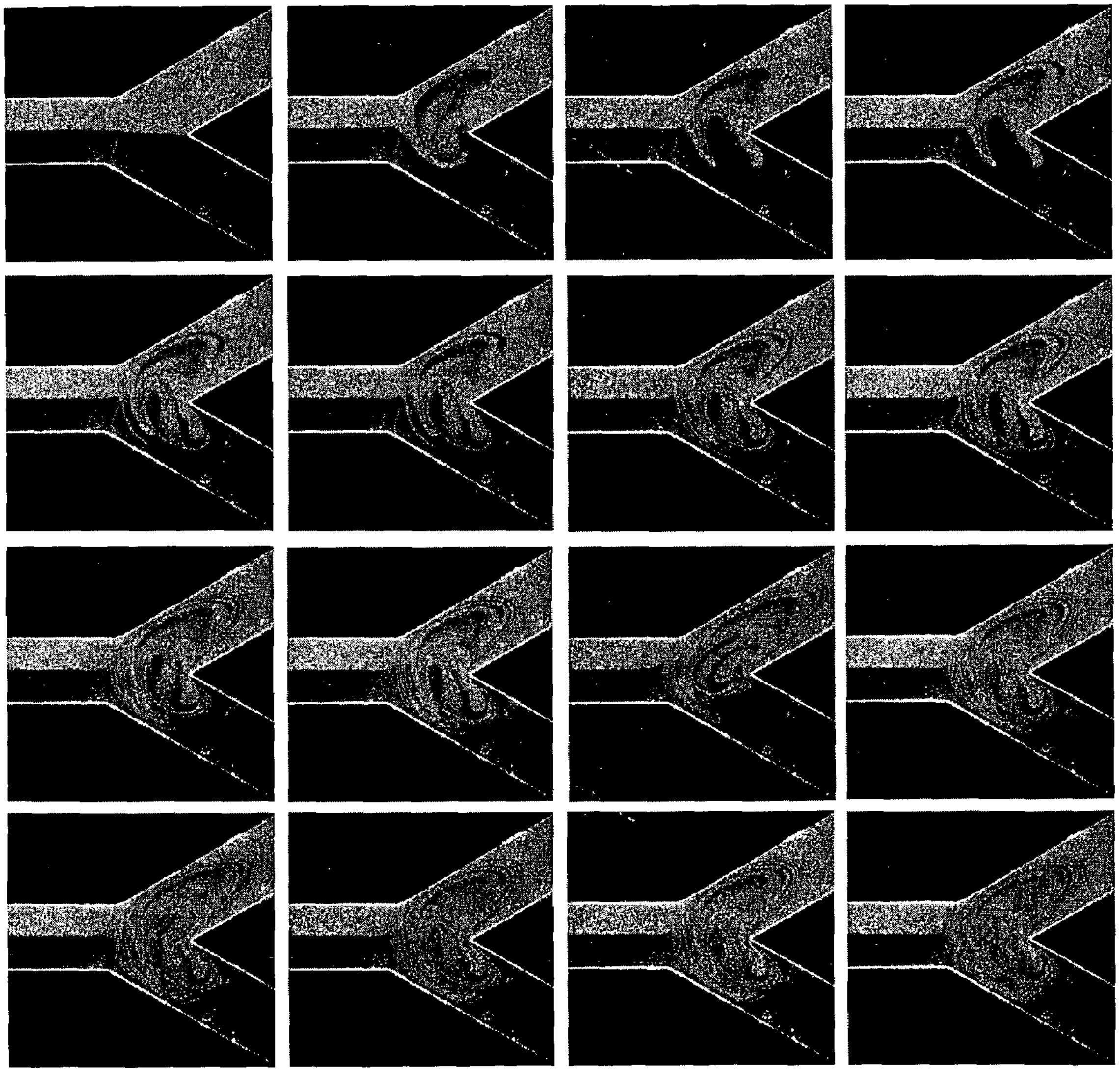
FIG. 14 shows startup of a mixing apparatus of the present invention incorporating pinch valves with no mean flow for the parameters described in pinch valve experiment 5 from Table I, with the non-dimensionalized times being 0.0, 0.282, 0.547, 0.922, 1.219, 1.500, 1.953, 2.250, 2.532, 2.985, 3.250, 3.532, 3.985, 4.266, 4.532, and 4.953 (read from top left across from left to right to bottom right)

Additional evidence supporting the existence of a chaotic region may be extracted from the analysis of the stationary (i.e., no mean flow) operation of the pinch valves, FIG. 14. The complex patterns formed by the tracer indicate stretching and folding of the mixing interface, eventually leading to a well-mixed flow.

EXAMPLE VI

Rigorous optimization of the pinch valve actuation parameters requires a quantitative measure of mixing. The information at hand suggests that image analysis should be used for this purpose, although other more direct means of quantification (such as cytometry) may also be considered.

The goal of the image analysis is to facilitate quantitative measurements of mixing in the flow by recovering the instantaneous concentration fields. First, the images are processed with a filter sensitive to gradient and structure size ("dust and scratch" filter). This filter removes small-scale (approximately 5 mum) intensity fluctuations due to slight non-uniformities in the tracer seeding. The size of the images is then reduced by a factor of 3, effectively smoothing the image further by anti-aliased downsampling. The lighting intensity varied from experiment to experiment, and it was therefore necessary to normalize the overall intensity of each image. The greyscale values of all pixels in the image were binned. The lowest and highest intensity bins that contained a set number of pixels were chosen as the minimum and maximum range limits. Intermediate greyscale values were scaled accordingly. Thus, occasional bright spots (for example, reflections from a bubble) were eliminated. This normalization is motivated by the interpretation of pixel intensity as local concentration of the material of the 'light' stream.

Figure 15:
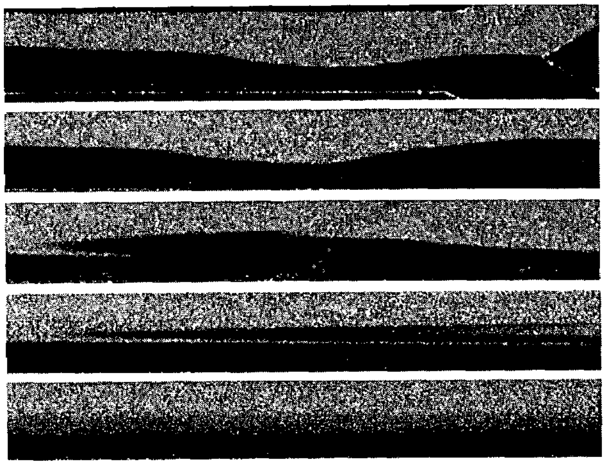
FIG. 15 shows histogram plots of peristaltic pump flow with accompanying pictures (on left) at different diameter lengths, with the diameter lengths (read from top to bottom) being at the Y-junction, 2 diameter lengths, 16 diameter lengths, 72 diameter lengths, and 180 diameter lengths.
Figure 15:
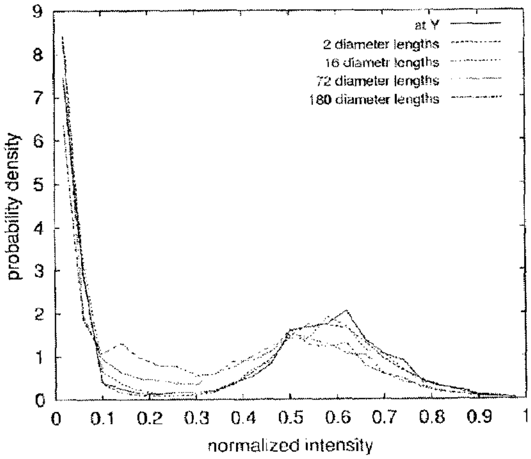

Histograms of greyscale values from the filtered images represent the probability density of finding a pixel at a given intensity. These are scaled so that the total probability is 1. Images for fully out of phase peristaltic flow at different distances downstream of the Y, accompanied by the respective histograms, are shown in FIG. 15. The histogram for the initial unmixed configuration (at the Y) shows a population of 'light' pixels and a somewhat more diffuse population of 'dark' pixels. These features persist further downstream, however an intermediate 'grey' population between the two emerges. This is fully consistent with the qualitative information contained in the images.

Figure 16:
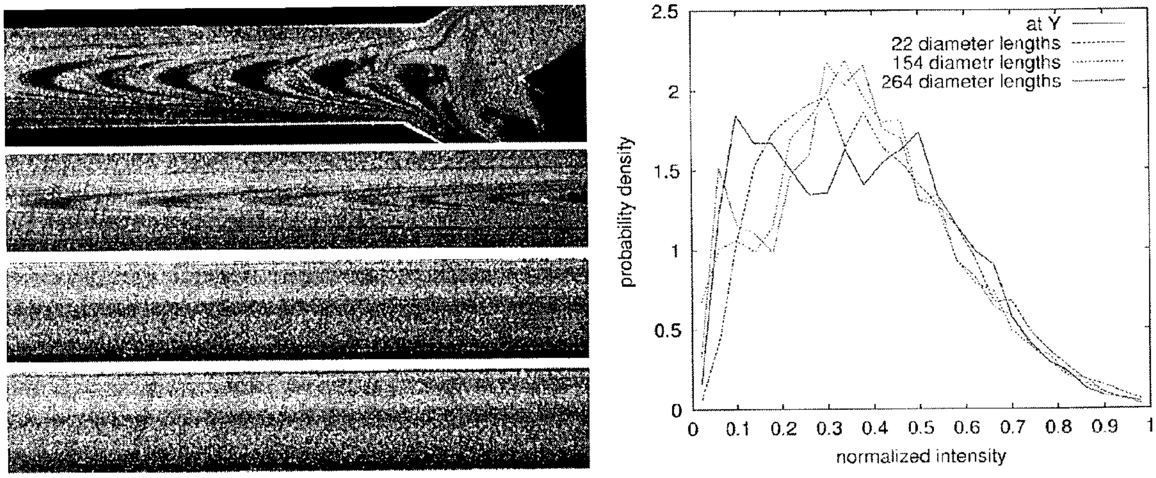
FIG. 16 shows histogram plots of experiment 5 from Table I, with accompanying pictures (on left) at different diameter lengths, with the diameter lengths (read from top to bottom) being at the Y-junction, 22 diameter lengths, 154 diameter lengths, and 264 diameter lengths.
Figure 17:
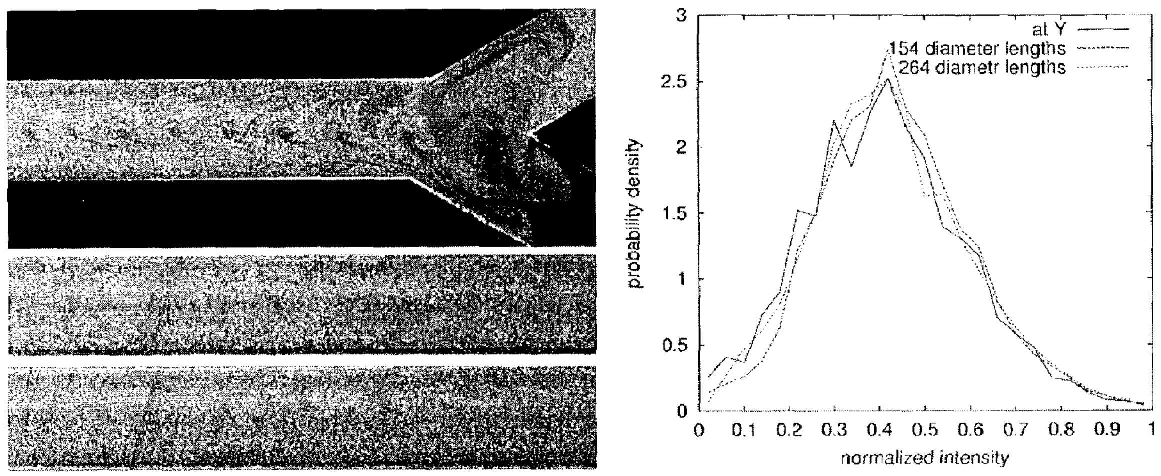
FIG. 17 shows histogram plots of experiment 4 from Table I, with accompanying pictures (on left) at different diameter lengths, with the diameter lengths (read from top to bottom) being at the Y-junction, 154 diameter lengths, and 264 diameter lengths.

Images and accompanying histograms for experiment 2 (from Table I) are shown in FIG. 16. The qualitative difference that may be discerned by inspection of the images is reflected in the histograms. The 'dark' population (the islands) is reflected in the lower peak in the histogram for x/d=0, accompanied by a diffuse 'light' peak. Because of the stretching action of the flow, the sharpness of the black peak is reduced as the flow proceeds downstream. Finally, the histogram for experiment 4 (from Table I), shown in FIG. 17, displays an almost indistinguishable black peak, which soon disappears. The histograms at x/d=154 and x/d=264 show an almost normal distribution, indicating complete mixing.

The correspondence in the qualitative features of the images and the corresponding histograms suggest that a 'mixing parameter' $M_1$ could be obtained from the histograms.

The first moment of the histogram (defined by the probability density p(x), where x is the greyscale value) about its centroid is defined as:

$$M_1 = \int_0^1 r \cdot p(x) dx, \quad (1)$$

where $r=|x-\bar{x}|$ and the centroid $\bar{x}$ is given by $$\bar{x} = \int_0^1 x \cdot p(x) dx, \quad (2)$$

Figure 18:
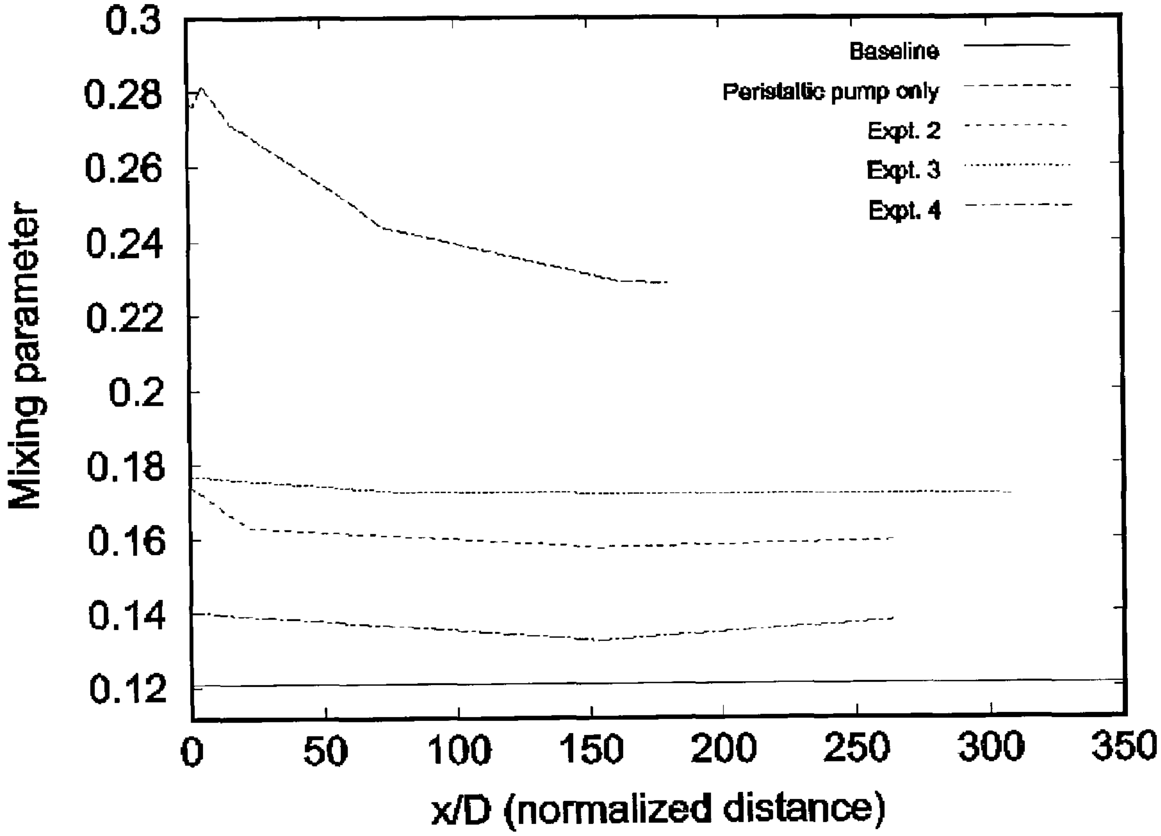
FIG. 18 shows a plot of mixing parameter as a function of distance past a Y-junction.

To establish a baseline for 'ideal' mixing, a normalized histogram plot was done on the image of a homogeneous section of seeded fluid, and used to determine a mixing parameter. At the opposite extreme, the mixing parameter for completely unmixed streams is found by taking the first moment of the histogram for a typical image of the peristaltic flow near the Y. The evolution of the mixing parameter for various experiments, as a function of distance from the Y connection, is plotted in FIG. 18. Clearly, the length of tube required to achieve steady-state conditions is much smaller with the pinch valves than with the peristaltic action alone. The baseline for ideal mixing is at $M_\infty=0.12$. The mixing parameter for unmixed flow is $M_0=0.28$. Using these, the percent fraction of ideal mixing for a given experiment is given by:

$$\Delta = 100 \times \frac{M_0 - M}{M_0 - M_\infty} \quad (3)$$

Table II shows the steady-state percentage mixing for the peristaltic pump and for different representative experiments.

TABLE II

Steady-state percent mixing for different experiments.

| Experiment | Best Mixing |
|---|---|
| Peristaltic Pump Only | 31% |
| Experiment 2 | 77% |
| Experiment 3 | 67% |
| Experiment 4 | 93% |
| Experiment 6 | 94% |

The mixing in experiment 2 is better than in experiment 3, although the period for experiment 2 is larger than for experiment 3. However, both pulse width and delay are smaller compared to the period in experiment 2. This shows that all timing parameters play a significant role in mixing behavior. The best mixing percentages for experiments 4 and 6 are similar, however the observed mixing for experiment 6 takes place just after the Y, 3-5 diameter lengths down the tube, whereas the maximum mixing achieved by experiment 4 appears to take longer.

The mixing enhancement in Table II appears to be closely connected to increased length of the mixing interface. The latter may be inferred from the flow images (post-processed as described above) as follows. For any intensity level, a corresponding intensity isocontour may be plotted. Its length varies with intensity (FIG. 19), however, within a considerable range of intensities (B to C) it remains nearly constant, with the corresponding isocontour largely retaining its appearance. The intensity range within which the boundary between 'light' and 'dark' streams is well-defined decreases with downstream distance because of diffusion, so the analysis of the interfacial properties concentrates on the immediate vicinity of the Y.

Figure 19:
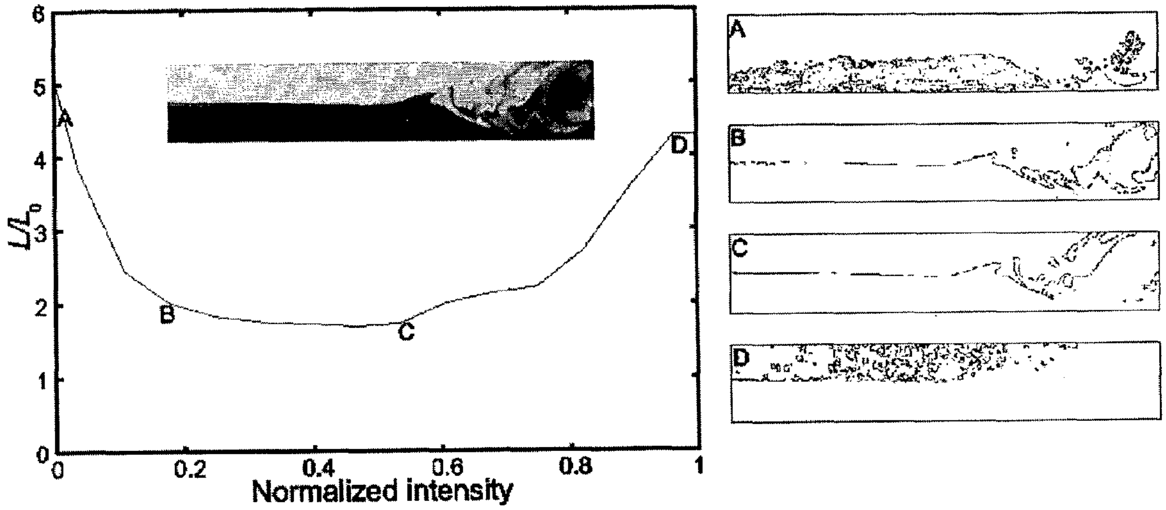
FIG. 19 shows lengths of normalized intensity isocontours for the fifth instantaneous image shown in FIG. 13 (experiment 5, dimensionless time 0.451), with the letter labels on the isocontours on the right corresponding to those on the graph.
Figure 20:
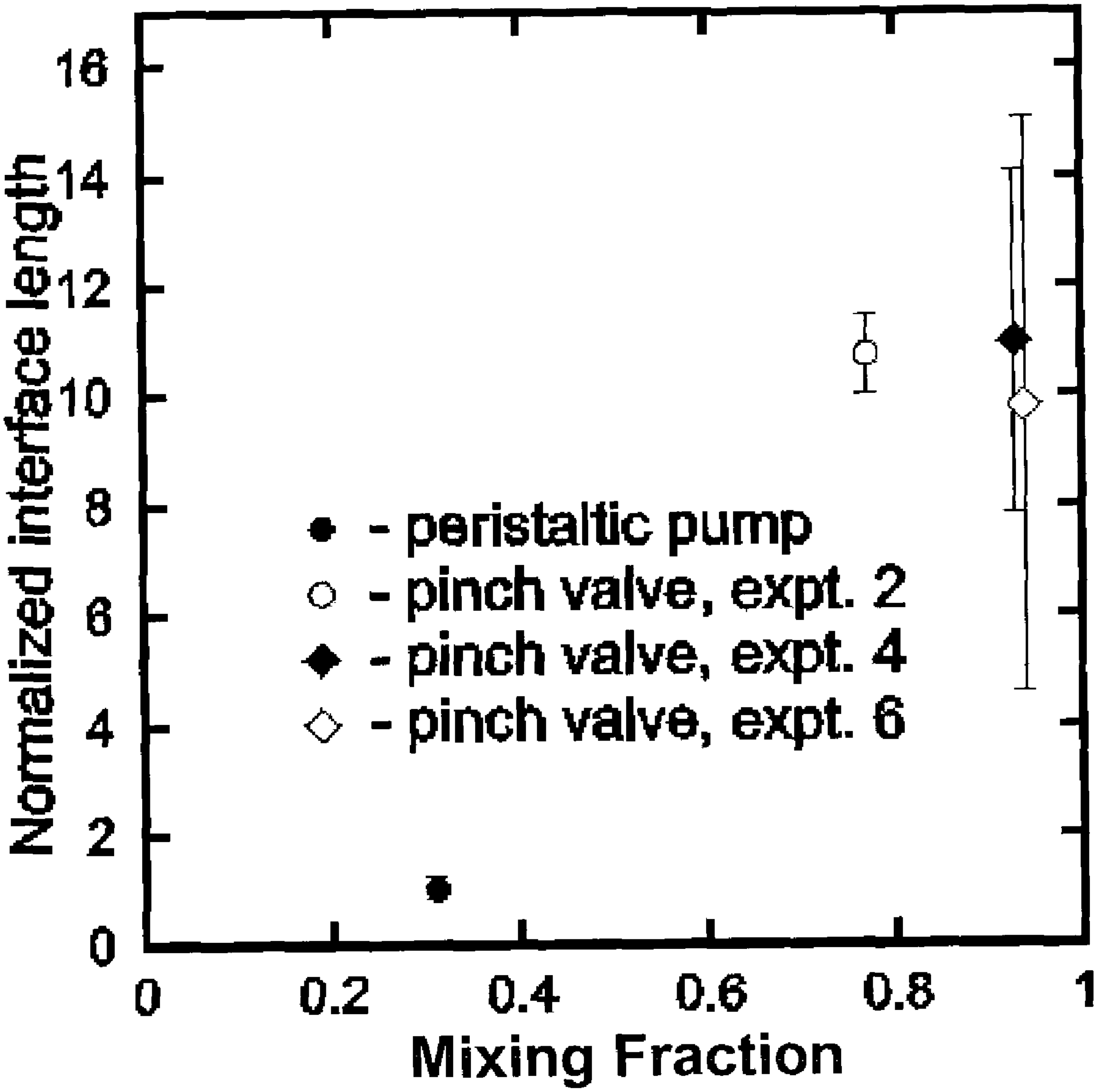
FIG. 20 shows normalized ensemble-averaged mixing interface length (vertical axis) versus steady-state mixing fraction (horizontal axis), with error bars denoting the standard deviation of ensemble-averaged results.

For the flow regimes investigated in the present invention, the middle of the intensity range between contours 'B' and 'C' as illustrated in FIG. 19 corresponds to normalized intensity of 0.35±0.05. This intensity value is selected to define the 'mixing interface' isocontour in the subsequent analysis. FIG. 20 shows the relationship between the steady-state interface length near the Y (ensemble-averaged over 12 images) and percentage mixing (Table II). The interface length is normalized by the length of the section visualized (5.3 diameters). There is a striking difference between the interface length for the peristaltic-pump flow and the pinch-valve driven flows. The overall trend the graph shows is for mixing quality to improve with the growth of interface length. However, the definition of the mixing interface illustrated in FIG. 19 fails in image areas with really good mixing (experiments 4 and 6), thus leading to less statistically reliable results for these flows.

EXAMPLE VII

Figure 21:
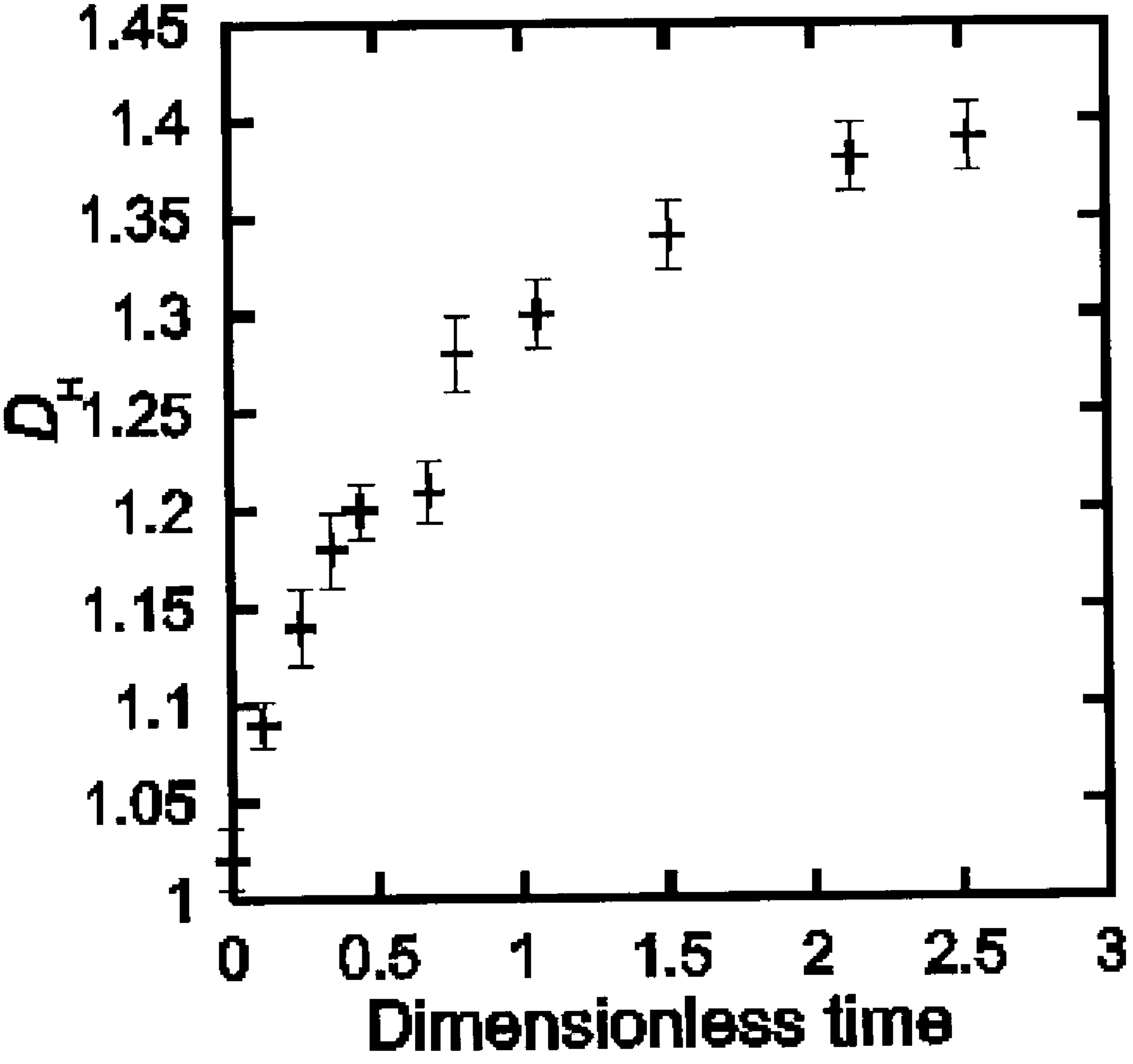
FIG. 21 shows a box-counting estimate of the fractal dimension $D_H$ of the mixing interface for the transient flow upon startup of a mixer according to the presenting invention using the parameters of experiment 5 from Table I, with error bars denoting the error of the fit used to extract the fractal dimension estimate.

The enhanced mixing in turbulent flows is strongly linked to complex interface geometry. The connection between fractals and turbulence was first suggested in the famous book, B. Mandelbrot, The fractal geometry of nature, W. H. Freeman, New York, 1982, and subsequent experiments in turbulent flows, such as described in K. R. Sreenivasan and C. Meneveau, The fractal facets of turbulence, Journal of Fluid Mechanics, 173:357-386 (1986), the entire contents and disclosures of which are hereby incorporated by reference, demonstrated a range of scales of the mixing interface to have fractal properties. Although the low-Reynolds number mixing flow described in the present invention is distinctly non-turbulent, enhanced mixing in it may also be associated with fractal interface geometry. To analyze this issue more closely, the fractal dimension of the mixing interface defined as described above is estimated. For the estimate of the Hausdorff dimension of the interface $D_H$, the box-counting procedure is employed as described in J. Theiler, Estimating fractal dimension, Journal of the Optical Society of America A—Optics and Image Science, 7:1055-1073 (1990), the entire contents and disclosure of which is hereby incorporated by reference. FIG. 21 shows the evolution of the interface fractal dimension for the transient startup flow shown in FIG. 13. A fractal dimension of 1 denotes a linear object, whereas two-dimensional sections of preturbulent and turbulent mixing interfaces are usually characterized by fractal dimensions between 1.3 and 1.4. The evolution of the fractal dimension for transient flow shows a simple trend: as the interface evolves from nearly-linear at early times to the highly-distorted steady-state morphology, the fractal dimension increases from unity to about 1.4, the latter value characterizing the steady-state.

Figure 22:
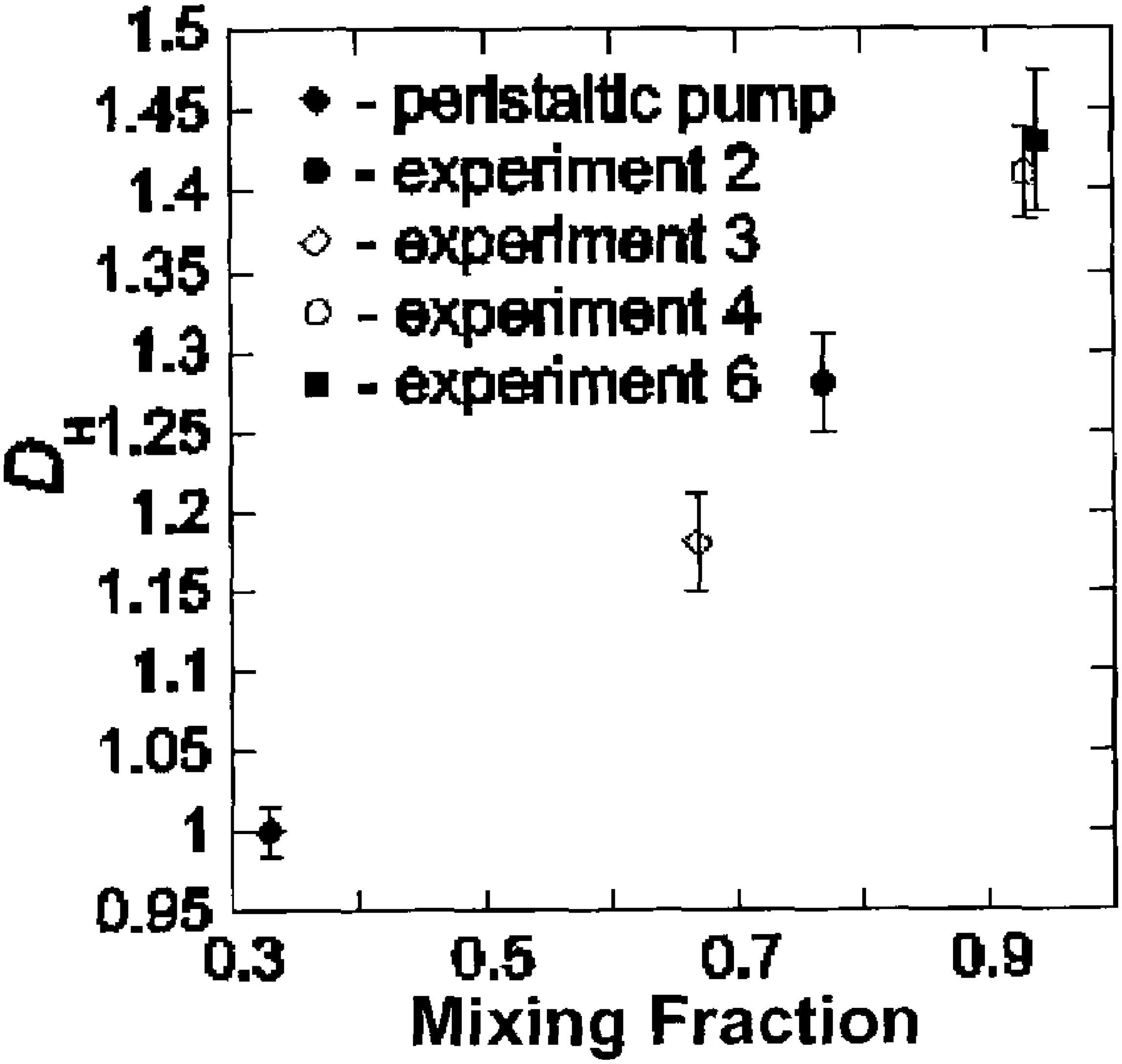
FIG. 22 shows a steady state fractal dimension $D_H$ estimate for the peristaltic-pump flow and flows in experiments 2, 3, 4 and 6 from Table I versus mixing fraction (see Table II), with measurements corresponding to specific experiments labeled in the graph.

FIG. 22 shows a comparison of some steady-state results for the peristaltic pump-driven flow and flows with the pinch valves. The relationship between the interface fractal dimension and the mixing quality as defined in Table II appears to be monotonic. In a sense, the interface fractal dimension is more strongly related to mixing than the interface length.

If the mean-flow component is absent (FIG. 14), the growth of the mixing-interface length initially follows a trend similar to that reported by Leong and Ottino, see C. Leong and J.

Figure 23:
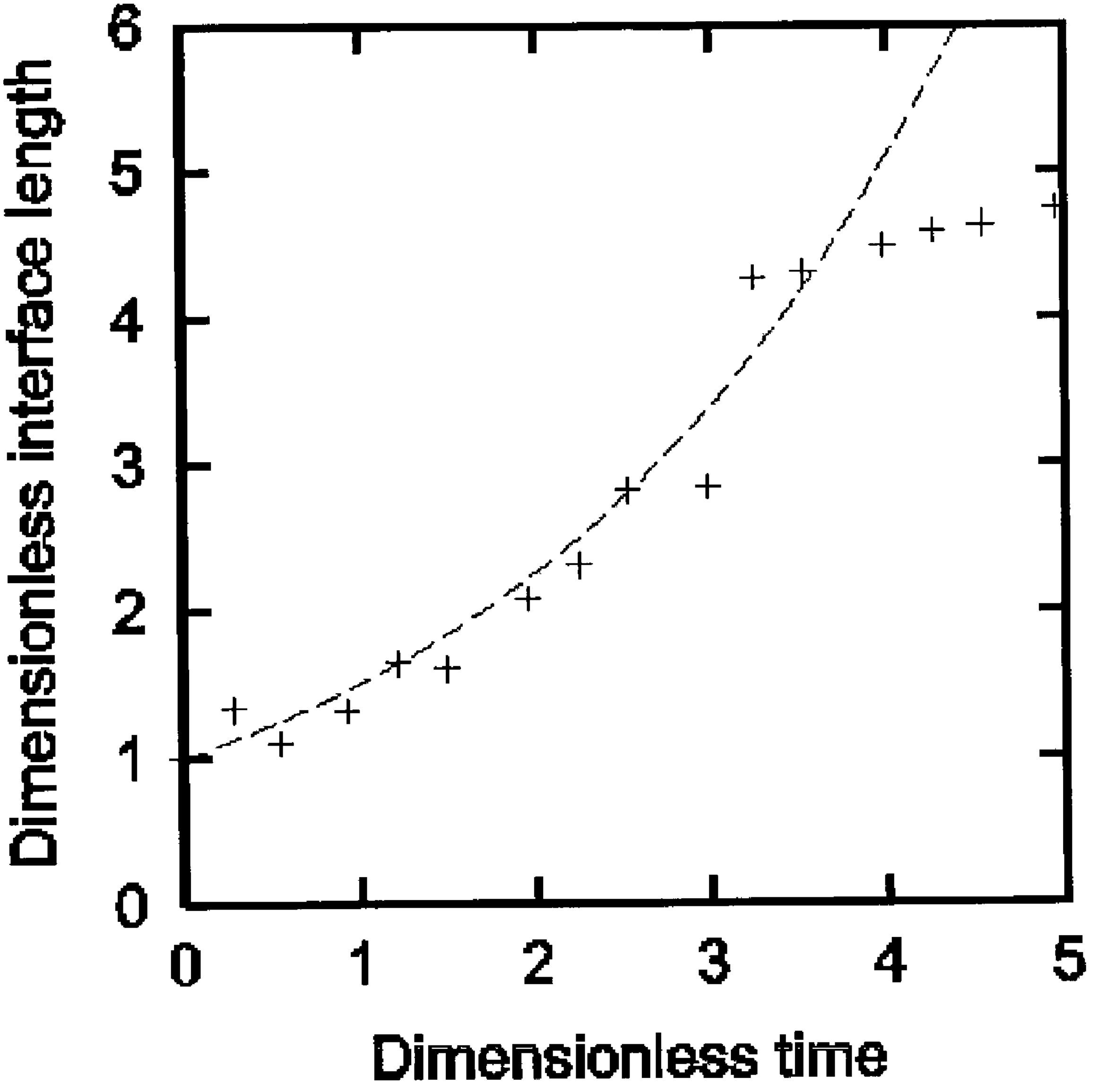
FIG. 23 shows normalized mixing interface length as the function of dimensionless time for pinch-valve controlled flow without the mean component, with the dashed line denoting exponential fit with exponent 0.407.

Ottino, Experiments on mixing due to chaotic advection in a cavity, Journal of Fluid Mechanics, 209:463-499 (1989), the entire contents and disclosure of which is hereby incorporated by reference, who observed exponential interface length growth in a low-Reynolds number chaotically mixing cavity flow. They also state that the exponent β in the expression for stretching $A=A_0 \exp(\beta t)$ can be construed as an average Liapunov exponent, positive value of the latter indicating chaotic flow character. The results presented in FIG. 23 are initially consistent with exponential growth (exponential fit denoted by dashed line). At late times, the mixing-interface tracing algorithm becomes unreliable—both due to interface striations thinning out beyond the resolution of the camera and due to the interface growing more diffuse. As the consequence of this, the measured mixing-interface length changes its trend of growth, asymptoting to a limit value dictated by the spatial and intensity-level limitations of the acquisition system. Prior to this stage, however, the fit with exponent β=0.407 describes the dependence of normalized mixing-interface length upon dimensionless time with a standard error of 2.6%. The formula used for curve-fitting is $l=\exp(\beta t)$, where l and t are dimensionless interface length and time. Only l values for t<3.9 were employed for fitting.

Many physical phenomena with a chaotic component (from turbulence to evolution) demonstrate fractal properties. The complex interface geometry of the flow driven by the pinch valves serves as evidence supporting the notion that the flow is chaotic. The boundary conditions applied to the flow are periodic, thus allowing construction of normalized intensity differences $$I_2^2 = \frac{\langle (I(x, y, t) - I(x, y, t+T))^2 \rangle}{\langle I(x, y, t)^2 \rangle},$$

where T is the driving period and the <•> operator denotes ensemble-averaging over several image pairs combined with spatial averaging. The closer the flow to periodic, the lower the $I_2^2$ value should be. To test this notion, comparisons were performed between the peristaltic-pump results and the results from experiment 6, with ensemble averaging over twelve T-separated image pairs and space averaging over the Y-section of the apparatus. The period T in the former case corresponds to the period of the interfacial wave caused by the peristaltic-pump action. In the case of the pinch-valve-driven flow, T is the period of the pinch valve cycle. The $I_2^2$ value for peristaltic-pump flow is 0.07±0.01, while for experiment 2 it is 0.27±0.02, showing a considerable increase in the temporal disorder. It is also of interest that changing the time delay between image pairs from T to 2T and 3T produces no significant change in the results.

All documents, patents, journal articles and other materials cited in the present application are hereby incorporated by reference.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method of mixing samples in-line in a microfluidic system, comprising:

introducing a first fluid sample into a flow-tube at a first end at a given velocity via a first conduit; and intermittently introducing a second fluid sample into said flow-tube at said first end, via a second conduit, wherein said first fluid sample and said second fluid sample converge in said flow tube to form an interface;

whereby said first fluid sample and said second fluid sample mix at said interface within said flow-tube, wherein fluid flow at said first end of said flow-tube is laminar and fluid flow at a second end of said flow-tube is laminar, and wherein said flow-tube has a constant diameter between said first end and said second end of said flow-tube.

2. The method of claim 1, wherein fluid flow through said flow-tube between said first end and said second end of said flow-tube is turbulent.

3. The method of claim 1, wherein the rate of mixing is not constant during progression of fluid flow in said flow-tube.

4. The method of claim 1, wherein intermittently introducing said second fluid sample includes operating a peristaltic pump.

5. The method of claim 1, wherein intermittently introducing said second fluid sample includes operating a pinch valve.

6. The method of claim 1, wherein said flow tube comprises an in-line micromixer to disturb fluid flow in said flow tube.

7. The method of claim 6, wherein fluid flow around said in-line micromixer is turbulent.

8. The method of claim 1, wherein said first fluid sample has a density different from said second fluid sample.

9. The method of claim 8, wherein said densities differ by at least 1%.

10. The method of claim 1, further comprising detecting reaction of the mixed fluids in-line via operation of an instrument.

11. The method of claim 10, wherein said instrument is a flow cytometer.

12. The method of claim 10, wherein said instrument is a luminescent detector.

13. The method of claim 10, wherein said instrument is a fluorescent detector.

14. The method of claim 10, further comprising analyzing the reaction of the fluids via operation of an instrument.

15. The method of claim 14, wherein said instrument is a flow cytometer.

16. The method of claim 1 wherein said given velocity is a first velocity and wherein the introducing of said second fluid sample into said flow tube includes introducing said second fluid sample at a second velocity, said second velocity being different from said first velocity, further comprising introducing a third fluid sample into said flow-tube at a third velocity via a third conduit.

17. The method of claim 16, wherein said third velocity is different from at least one of said first velocity and said second velocity.

18. The method of claim 16, wherein said third fluid sample is introduced into said flow-tube at the first end of said flow-tube.

19. The method of claim 16, wherein said third fluid sample is introduced into said flow-tube between said first end and said second end of said flow-tube.

20. A microfluidic apparatus for mixing samples in-line, comprising:

first means for introducing a first fluid sample into a flow-tube at a first end at a given velocity via a first conduit; and second means for intermittently introducing a second fluid sample into said flow-tube at said first end via a second conduit, wherein said first fluid sample and said second fluid sample converge in said flow tube to form an interface;

whereby said first fluid sample and said second fluid sample mix at said interface within said flow-tube, wherein fluid flow at said first end of said flow-tube is laminar and fluid flow at a second end of said flow-tube is laminar, and wherein said flow-tube has a constant diameter between said first end and said second end of said flow-tube.

21. The apparatus of claim 20, further comprising means for controlling fluid flow through said first conduit and said second conduit.

22. The apparatus of claim 20, wherein said means for controlling fluid flow comprises pinch valves.

23. The apparatus of claim 20 wherein said means for intermittently introducing said second fluid sample into said flow-tube includes a peristaltic pump.

24. The apparatus of claim 20 wherein said given velocity is a first velocity and wherein said second means introduces said second fluid sample into said flow-tube at a second velocity different from said first velocity.

* * * * *

UNITED STATES PATENT AND TRADEMARK OFFICE

CERTIFICATE OF CORRECTION

PATENT NO. : 7,416,903 B2
APPLICATION NO. : 10/428931
DATED : August 26, 2008
INVENTOR(S) : Larry A. Sklar et al.

It is certified that error appears in the above-identified patent and that said Letters Patent is hereby corrected as shown below:

Column 1, lines 29-32, change "This invention is made with government support under Grant Number GM60799/EB00264 awarded by the National Institutes of Health. The government may have certain rights in this invention." to --This invention was made with government support under Grant no. GM060799/EB000264 awarded by the National Institutes of Health. The government has certain rights in this invention.--

Signed and Sealed this

Eleventh Day of November, 2008

JON W. DUDAS
*Director of the United States Patent and Trademark Office*